United States Patent [19]
Liu et al.

[11] Patent Number: 5,968,793
[45] Date of Patent: *Oct. 19, 1999

[54] SPECIFIC GENE ACTIVATION BY CHIMERIC GAL4 TRANSCRIPTION FACTORS IN STABLE TRANSGENIC PLANTS

[75] Inventors: Zhan-Bin Liu, Greenville, Del.; Joan Tellefsen Odell, Unionville, Pa.

[73] Assignee: E. I. du Pont de Nemours and Company, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 08/881,687

[22] Filed: Jun. 24, 1997

[51] Int. Cl.$^6$ .............................. C12N 5/14; C12N 15/90; A01H 1/04; A01H 5/10

[52] U.S. Cl. ...................... 435/172.3; 435/419; 800/205; 800/250

[58] Field of Search ............................... 435/69.1, 172.1, 435/172.3, 320.1, 410, 419; 800/205, 250; 935/35, 36, 67

[56] References Cited

U.S. PATENT DOCUMENTS 5,409,823  4/1995  Crossland et al. .................... 435/172.3

FOREIGN PATENT DOCUMENTS 2150039    8/1996  Canada .
0 589 841 A2  3/1994  European Pat. Off. .
97/30164   8/1997  WIPO .

OTHER PUBLICATIONS

R.J. Wilde et al., Control of gene expression in plant cells using a 434:VP16 chimeric protein, *Plant Molecular Biology*, 24, 381–388, 1994.

S.J. Triezenberg et al., Functional dissection of VP16, the transactivator of herpes simplex virus immediate early gene expression, *Genes & Development*, 2, 718–729, 1988.

J. Ma et al., Yeast activators stimulate plant gene expression, *Nature*, 334, 631–633, Aug. 1988.

A.J. Bobb et al., PvAlf, an embryo–specific acidic transcriptional activator enhances gene expression from phaseolin and phytohemagglutinin promoters, *The Plant Journal*, 8(3), 331–343, 1995.

J. Ma et al., Deletion Analysis of GAL4 Defines Two Transcriptional Activating Segments, *Cell*, 48, 847–853, Mar. 13, 1987.

T. Aoyama et al., A glucocorticoid–mediated transcriptional inducation system in transgenic plants, *The Plant Journal*, 11(3), 605–612, 1997.

C. Reichel et al., Inefficient expression of the DNA–binding domain of GAL4 in transgenic plants, *Plant Cell Report*, 14, 773–776, 1995.

U. Schindler et al., DNA binding site preferences and transcriptional activation properties of the Arabidopsis transcription factor GBF1, *The EABO Journal*, 11, 1275–1289, 1992.

A.H.M. van der Geest, The β–phaseolin gene is flanked by matrix attachment regions, *Plant Journal*, 6(3), 413–423, 1994.

A.H.M. van der Geese, The β–phaseolin 5' matrix attachment region acts as an enhancer facilitator, *Plant Molecular Biology*, 33, 553–557, 1997.

*Primary Examiner*—Nancy Degen
*Assistant Examiner*—Thomas G. Larson

[57] ABSTRACT

A method for regulating gene expression in a stably transformed transgenic plant cell utilizing a Gal4 chimeric transcription factor is described.

10 Claims, 21 Drawing Sheets

5,968,793

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:1:

CGGAGGACAG TCCTCCG                      17

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (xi) SEQUENCE DESCRIPTION: SEQ ID NO:2:

CGGATTAGAA GCCGCCG                      17

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (xi) SEQUENCE DESCRIPTION: SEQ ID NO:3:

```
CGGGTGACAG CCCTCCG                                                      17
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (xi) SEQUENCE DESCRIPTION: SEQ ID NO:4:

```
AGGAAGACTC TCCTCCG                                                      17
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Saccharomyces cerevisiae (xi) SEQUENCE DESCRIPTION: SEQ ID NO:5:

```
CGCGCCGCAC TGCTCCG                                                      17
```

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Saccharomyces cerevisiae (xi) SEQUENCE DESCRIPTION: SEQ ID NO:6:

```
CGGACAACTG TTGACCG                                                      17
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "RY-G-box-RY element"

(iii) HYPOTHETICAL: YES (xi) SEQUENCE DESCRIPTION: SEQ ID NO:7:

```
CATGCATGTC TACACGTGAT CGCCATGCAA                                        30
```

(2) INFORMATION FOR SEQ ID NO:8:

(i) SEQUENCE CHARACTERISTICS:
        (A) LENGTH:  7 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (ix) FEATURE:
        (A) NAME/KEY:  misc_binding
        (B) LOCATION:  1..6
        (D) OTHER INFORMATION:  /function= "CACA box"

(xi) SEQUENCE DESCRIPTION:  SEQ ID NO:8:

TAACACA                                                                         7

(2) INFORMATION FOR SEQ ID NO:9:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (xi) SEQUENCE DESCRIPTION:  SEQ ID NO:9:

TTCCATAGCC ATGCATACTG AATGTCT                                                   27

(2) INFORMATION FOR SEQ ID NO:10:

(i) SEQUENCE CHARACTERISTICS:
        (A) LENGTH:  8 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (xi) SEQUENCE DESCRIPTION:  SEQ ID NO:10:

CATGCATG                                                                        8

(2) INFORMATION FOR SEQ ID NO:11:

(i) SEQUENCE CHARACTERISTICS:
        (A) LENGTH:  8 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (xi) SEQUENCE DESCRIPTION:  SEQ ID NO:11:

CATGCAAG                                                                        8

(2) INFORMATION FOR SEQ ID NO:12:

(i) SEQUENCE CHARACTERISTICS:
        (A) LENGTH:  8 base pairs
        (B) TYPE:  nucleic acid
        (C) STRANDEDNESS:  single (D) TOPOLOGY:  linear (ii) MOLECULE TYPE:  DNA (genomic)

(iii) HYPOTHETICAL:  NO (xi) SEQUENCE DESCRIPTION:  SEQ ID NO:12:

CATGCATA                                                                                         8

(2) INFORMATION FOR SEQ ID NO:13:

(i) SEQUENCE CHARACTERISTICS:
        (A) LENGTH:  43 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (ix) FEATURE:
        (A) NAME/KEY:  misc_feature
        (B) LOCATION:  1..7
        (D) OTHER INFORMATION:  /standard_name= "CACA box"

(ix) FEATURE:
        (A) NAME/KEY:  misc_feature
        (B) LOCATION:  14..43
        (D) OTHER INFORMATION:  /standard_name= "legumin box"

(xi) SEQUENCE DESCRIPTION:  SEQ ID NO:13:

TAACACACAA GGCTTCCATA GCCATGCATA CTGAAGAATG TCT                                                   3

(2) INFORMATION FOR SEQ ID NO:14:

(i) SEQUENCE CHARACTERISTICS:
        (A) LENGTH:  11 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (xi) SEQUENCE DESCRIPTION:  SEQ ID NO:14:

GGACACGTGG C                                                                                     1

(2) INFORMATION FOR SEQ ID NO:15:

(i) SEQUENCE CHARACTERISTICS:
        (A) LENGTH:  9 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (xi) SEQUENCE DESCRIPTION:  SEQ ID NO:15:

CGAGCAGGC                                                                                        9

(2) INFORMATION FOR SEQ ID NO:16:

(i) SEQUENCE CHARACTERISTICS:
        (A) LENGTH:  11 base pairs
        (B) TYPE:  nucleic acid
        (C) STRANDEDNESS:  single
        (D) TOPOLOGY:  linear

```
        (ii) MOLECULE TYPE:  DNA (genomic)

(iii) HYPOTHETICAL:  NO (xi) SEQUENCE DESCRIPTION:  SEQ ID NO:16:

GCACACGTGC C                                                                    1

(2) INFORMATION FOR SEQ ID NO:17:

(i) SEQUENCE CHARACTERISTICS:
             (A) LENGTH:  67 base pairs
             (B) TYPE:  nucleic acid
             (C) STRANDEDNESS:  single
             (D) TOPOLOGY:  linear (ii) MOLECULE TYPE:  DNA (genomic)

(iii) HYPOTHETICAL:  NO (ix) FEATURE:
             (A) NAME/KEY:  misc_feature
             (B) LOCATION:  1..11
             (D) OTHER INFORMATION:  /standard_name= "Em1a element"

(ix) FEATURE:
             (A) NAME/KEY:  misc_feature
             (B) LOCATION:  28..36
             (D) OTHER INFORMATION:  /standard_name= "Em2 element"

(ix) FEATURE:
             (A) NAME/KEY:  misc_feature
             (B) LOCATION:  57..67
             (D) OTHER INFORMATION:  /standard_name= "Em1b element"

(xi) SEQUENCE DESCRIPTION:  SEQ ID NO:17:

GGACACGTGG CGCGACAGCA GGGACAACGA GCAGGCCGAC GCACGTCCGC GTCGCTGCAC              60

ACGTGCC                                                                        67

(2) INFORMATION FOR SEQ ID NO:18:

(i) SEQUENCE CHARACTERISTICS:
             (A) LENGTH:  24 base pairs
             (B) TYPE:  nucleic acid
             (C) STRANDEDNESS:  single
             (D) TOPOLOGY:  linear (ii) MOLECULE TYPE:  DNA (genomic)

(iii) HYPOTHETICAL:  NO (xi) SEQUENCE DESCRIPTION:  SEQ ID NO:18:

GTGTCGTGTC GTCCATGCAT GCAC                                                     24

(2) INFORMATION FOR SEQ ID NO:19:

(i) SEQUENCE CHARACTERISTICS:
             (A) LENGTH:  10 base pairs
             (B) TYPE:  nucleic acid
             (C) STRANDEDNESS:  single
             (D) TOPOLOGY:  linear (ii) MOLECULE TYPE:  DNA (genomic)

(iii) HYPOTHETICAL:  NO (ix) FEATURE:
             (A) NAME/KEY:  misc_feature
             (B) LOCATION:  2..8
             (D) OTHER INFORMATION:  /standard_name= "G-box motif"

(xi) SEQUENCE DESCRIPTION:  SEQ ID NO:19:

TCCACGTGGC                                                                     10
```

(2) INFORMATION FOR SEQ ID NO:20:

(i) SEQUENCE CHARACTERISTICS:
        (A) LENGTH:  10 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  YES (ix) FEATURE:
        (A) NAME/KEY:  misc_feature
        (B) LOCATION:  2..7
        (D) OTHER INFORMATION:  /standard_name= "G-box element"

(xi) SEQUENCE DESCRIPTION:  SEQ ID NO:20:

CCACGTGGCC                                                              10

(2) INFORMATION FOR SEQ ID NO:21:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (ix) FEATURE:
        (A) NAME/KEY:  misc_feature
        (B) LOCATION:  2..7

(xi) SEQUENCE DESCRIPTION:  SEQ ID NO:21:

CGGATTAGAA GCCGCCG                                               17

(2) INFORMATION FOR SEQ ID NO:22:

(i) SEQUENCE CHARACTERISTICS:
        (A) LENGTH:  38 base pairs
        (B) TYPE:  nucleic acid
        (C) STRANDEDNESS:  single
        (D) TOPOLOGY:  linear (ii) MOLECULE TYPE:  DNA (genomic)

(iii) HYPOTHETICAL:  NO (ix) FEATURE:
        (A) NAME/KEY:  misc_feature
        (B) LOCATION:  2..7
        (D) OTHER INFORMATION:  /standard_name= "G-box motif"

(xi) SEQUENCE DESCRIPTION:  SEQ ID NO:22:

CCACGTGGCC ATCCGGTGGC CGTCCCTCCA ACCTAACC                      38

(2) INFORMATION FOR SEQ ID NO:23:

(i) SEQUENCE CHARACTERISTICS:
        (A) LENGTH:  119 base pairs
        (B) TYPE:  nucleic acid
        (C) STRANDEDNESS:  single
        (D) TOPOLOGY:  linear (ii) MOLECULE TYPE:  other nucleic acid
        (A) DESCRIPTION:  /desc = "oligonucleotide"

(iii) HYPOTHETICAL:  NO

```
    (ix) FEATURE:
         (A) NAME/KEY:  protein_bind
         (B) LOCATION:  14..30
         (D) OTHER INFORMATION:  /bound_moiety= "Gal4 biding domain"

(ix) FEATURE:
         (A) NAME/KEY:  protein_bind
         (B) LOCATION:  36..52
         (D) OTHER INFORMATION:  /bound_moiety= "Gal4 binding domain"

(ix) FEATURE:
         (A) NAME/KEY:  protein_bind
         (B) LOCATION:  64..80
         (D) OTHER INFORMATION:  /bound_moiety= "Gal4 binding domain"

(ix) FEATURE:
         (A) NAME/KEY:  protein_bind
         (B) LOCATION:  86..102
         (D) OTHER INFORMATION:  /bound_moiety= "Gal4 binding domain"

(xi) SEQUENCE DESCRIPTION:  SEQ ID NO:23:

TCACCGGATC CTACGGAGGA CAGTCCTCCG ATTTACGGAG GACAGTCCTC CGAATATCGA        60

TAACGGAGGA CAGTCCTCCG ATTTACGGAG GACAGTCCTC CGAATTATCT GCAGAATAA       119

(2) INFORMATION FOR SEQ ID NO:24:

(i) SEQUENCE CHARACTERISTICS:
         (A) LENGTH:  119 base pairs
         (B) TYPE:  nucleic acid
         (C) STRANDEDNESS:  single
         (D) TOPOLOGY:  linear (ii) MOLECULE TYPE:  other nucleic acid
         (A) DESCRIPTION:  /desc = "oligonucleotide"

(iii) HYPOTHETICAL:  NO (ix) FEATURE:
         (A) NAME/KEY:  protein_bind
         (B) LOCATION:  18..34
         (D) OTHER INFORMATION:  /bound_moiety= "Gal4 binding domain"

(ix) FEATURE:
         (A) NAME/KEY:  protein_bind
         (B) LOCATION:  40..56
         (D) OTHER INFORMATION:  /bound_moiety= "Gal4 binding domain"

(ix) FEATURE:
         (A) NAME/KEY:  protein_bind
         (B) LOCATION:  68..84
         (D) OTHER INFORMATION:  /bound_moiety= "Gal4 binding domain"

(ix) FEATURE:
         (A) NAME/KEY:  protein_bind
         (B) LOCATION:  90..106
         (D) OTHER INFORMATION:  /bound_moiety= "Gal4 binding domain"

(xi) SEQUENCE DESCRIPTION:  SEQ ID NO:24:

TTATTCTGCA GATAATTCGG AGGACTGTCC TCCGTAAATC GGAGGACTGT CCTCCGTTAT        60

CGATATTCGG AGGACTGTCC TCCGTAAATC GGAGGACTGT CCTCCGTAGG ATCCGGTGA       119

(2) INFORMATION FOR SEQ ID NO:25:

(i) SEQUENCE CHARACTERISTICS:
         (A) LENGTH:  113 base pairs
         (B) TYPE:  nucleic acid
         (C) STRANDEDNESS:  single
         (D) TOPOLOGY:  linear (ii) MOLECULE TYPE:  other nucleic acid
         (A) DESCRIPTION:  /desc = "oligonucleotide"

(iii) HYPOTHETICAL:  NO
```

```
    (ix) FEATURE:
         (A) NAME/KEY:  misc_feature
         (B) LOCATION:  8..37
         (D) OTHER INFORMATION:/standard_name= "RY-G-box-RY
             element"

(ix) FEATURE:
         (A) NAME/KEY:  misc_feature
         (B) LOCATION:  82..111
         (D) OTHER INFORMATION:/standard_name= "RY-G-box-RY
             element"

(xi) SEQUENCE DESCRIPTION:  SEQ ID NO:25:

GATCCTGCAT GCATGTCTAC ACGTGATCGC CATGCAATTT GGCTCACCCC TCGAGCTGCA      60

GTAGCATGCT TCAGTCTGTT GCATGCATGT CTACACGTGA TCGCCATGCA ATT           113

(2) INFORMATION FOR SEQ ID NO:26:

(i) SEQUENCE CHARACTERISTICS:
         (A) LENGTH:  113 base pairs
         (B) TYPE:  nucleic acid
         (C) STRANDEDNESS:  single
         (D) TOPOLOGY:  linear (ii) MOLECULE TYPE:  other nucleic acid
         (A) DESCRIPTION:  /desc = "oligonucleotide"

(iii) HYPOTHETICAL:  NO (ix) FEATURE:
         (A) NAME/KEY:  misc_feature
         (B) LOCATION:  7..36
         (D) OTHER INFORMATION:/standard_name= "RY-G-box-RY
             element"

(ix) FEATURE:
         (A) NAME/KEY:  misc_feature
         (B) LOCATION:  81..110
         (D) OTHER INFORMATION:/standard_name= "RY-G-box-RY
             element"

(xi) SEQUENCE DESCRIPTION:  SEQ ID NO:26:

GATCAATTGC ATGGCGATCA CGTGTAGACA TGCATGCAAC AGACTGAAGC ATGCTACTGC      60

AGCTCGAGGG GTAGGCCAAA TTGCATGGCG ATCACGTGTA GACATGCATG CAG           113

(2) INFORMATION FOR SEQ ID NO:27:

(i) SEQUENCE CHARACTERISTICS:
         (A) LENGTH:  143 base pairs
         (B) TYPE:  nucleic acid
         (C) STRANDEDNESS:  single
         (D) TOPOLOGY:  linear (ii) MOLECULE TYPE:  other nucleic acid
         (A) DESCRIPTION:  /desc = "oligonucleotide"

(iii) HYPOTHETICAL:  NO (ix) FEATURE:
         (A) NAME/KEY:  misc_feature
         (B) LOCATION:  9..51
         (D) OTHER INFORMATION:  /standard_name= "Gy2 element"

(ix) FEATURE:
         (A) NAME/KEY:  misc_feature
         (B) LOCATION:  98..140
         (D) OTHER INFORMATION:  /standard_name= "Gy2 element"

(xi) SEQUENCE DESCRIPTION:  SEQ ID NO:27:

GATCCGTGTA ACACACAAGG CTTCCATAGC CATGCATACT GAAGAATGTC TCAATGGCTC      60

ACCCCTCGAG CTGCAGTAGC ATGCTTCAGT CTGTGTGTAA CACACAAGGC TTCCATAGCC    120
```

```
ATGCATACTG AAGAATGTCT CAA                                                    143

(2) INFORMATION FOR SEQ ID NO:28:

(i) SEQUENCE CHARACTERISTICS:
          (A) LENGTH: 143 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(iii) HYPOTHETICAL: NO (ix) FEATURE:
          (A) NAME/KEY: misc_binding
          (B) LOCATION: 8..50
          (D) OTHER INFORMATION: /standard_name= "Gy2 element"

(ix) FEATURE:
          (A) NAME/KEY: misc_feature
          (B) LOCATION: 97..139
          (D) OTHER INFORMATION: /standard_name= "Gy2 element"

(xi) SEQUENCE DESCRIPTION: SEQ ID NO:28:

GATCTTGAGA CATTCTTCAG TATGCATGGC TATGGAAGCC TTGTGTGTTA CACACAGACT             60

GAAGCATGCT ACTGCAGCTC GAGGGGTGAG CCATTGAGAC ATTCTTCAGT ATGCATGGCT            120

ATGGAAGCCT TGTGTGTTAC ACG                                                   143

(2) INFORMATION FOR SEQ ID NO:29:

(i) SEQUENCE CHARACTERISTICS:
          (A) LENGTH: 195 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(iii) HYPOTHETICAL: NO (ix) FEATURE:
          (A) NAME/KEY: misc_feature
          (B) LOCATION: 10..76
          (D) OTHER INFORMATION:/standard_name= "Em regulatory
              element"

(ix) FEATURE:
          (A) NAME/KEY: misc_feature
          (B) LOCATION: 125..191
          (D) OTHER INFORMATION:/standard_name= "Em regulatory
              element"

(xi) SEQUENCE DESCRIPTION: SEQ ID NO:29:

GATCCTGCCG GACACGTGGC GCGACAGCAG GGACAACGAG CAGGCCGACG CACGTCCGCG             60

TCGCTGCACA CGTGCCGCCT TGGCTCACCC CTCGAGCTGC AGTAGCATGC TTCAGTCTGT            120

TGCCGGACAC GTGGCGCGAC AGCAGGGACA ACGAGCAGGC CGACGCACGT CCGCGTCGCT             80

GCACACGTGC CGCCT                                                            195

(2) INFORMATION FOR SEQ ID NO:30:

(i) SEQUENCE CHARACTERISTICS:
          (A) LENGTH: 195 base pairs
          (B) TYPE: nucleic acid
          (C) STRANDEDNESS: single
          (D) TOPOLOGY: linear (ii) MOLECULE TYPE: other nucleic acid
```

(A) DESCRIPTION:  /desc = "oligonucleotide"

(iii) HYPOTHETICAL:  NO (ix) FEATURE:
        (A) NAME/KEY:  misc_feature
        (B) LOCATION:  9..75
        (D) OTHER INFORMATION:/standard_name= "Em regulatory
            element"

(ix) FEATURE:
        (A) NAME/KEY:  misc_feature
        (B) LOCATION:  124..190
        (D) OTHER INFORMATION:/standard_name= "Em regulatory
            element"

(xi) SEQUENCE DESCRIPTION:  SEQ ID NO:30:

GATCAGGCGG CACGTGTGCA GCGACGCGGA CGTGCGTCGG CCTGCTCGTT GTCCCTGCTG    60

TCGCGCCACG TGTCCGGCAA CAGACTGAAG CATGCTACTG CAGCTCGAGG GGTGAGCCAA   120

GGCGGCACGT GTGCAGCGAC GCGGACGTGC GTCGGCCTGC TCGTTGTCCC TGCTGTCGCG    80

CCACGTGTCC GGCAG                                                   195

(2) INFORMATION FOR SEQ ID NO:31:

(i) SEQUENCE CHARACTERISTICS:
        (A) LENGTH:  105 base pairs
        (B) TYPE:  nucleic acid
        (C) STRANDEDNESS:  single
        (D) TOPOLOGY:  linear (ii) MOLECULE TYPE:  other nucleic acid
        (A) DESCRIPTION:  /desc = "oligonucleotide"

(iii) HYPOTHETICAL:  NO (ix) FEATURE:
        (A) NAME/KEY:  misc_feature
        (B) LOCATION:  9..32
        (D) OTHER INFORMATION:/standard_name= "C1 regulatory
            element"

(ix) FEATURE:
        (A) NAME/KEY:  misc_feature
        (B) LOCATION:  79..102
        (D) OTHER INFORMATION:/standard_name= "C1 regulatory
            element"

(xi) SEQUENCE DESCRIPTION:  SEQ ID NO:31:

GATCCGCAGT GTCGTGTCGT CCATGCATGC ACTTTTGGCT CACCCCTCGA GCTGCAGTAG    60

CATGCTTCAG TCTGTGCAGT GTCGTGTCGT CCATGCATGC ACTTT                  105

(2) INFORMATION FOR SEQ ID NO:32:

(i) SEQUENCE CHARACTERISTICS:
        (A) LENGTH:  105 base pairs
        (B) TYPE:  nucleic acid
        (C) STRANDEDNESS:  single
        (D) TOPOLOGY:  linear (ii) MOLECULE TYPE:  other nucleic acid
        (A) DESCRIPTION:  /desc = "oligonucleotide"

(iii) HYPOTHETICAL:  NO (ix) FEATURE:
        (A) NAME/KEY:  misc_feature
        (B) LOCATION:  8..31
        (D) OTHER INFORMATION:/standard_name= "C1 regulatory
            element"

(ix) FEATURE:
        (A) NAME/KEY:  misc_feature

```
          (B) LOCATION: 78..101
          (D) OTHER INFORMATION:/standard_name= "C1 regulatory
              element"

(xi) SEQUENCE DESCRIPTION: SEQ ID NO:32:

GATCAAAGTG CATGCATGGA CGACACGACA CTGCACAGAC TGAAGCATGC TACTGCAGCT    60

CGAGGGGTGA GCCAAAAGTG CATGCATGGA CGACACGACA CTGCG                   105

(2) INFORMATION FOR SEQ ID NO:33:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (ix) FEATURE:
        (A) NAME/KEY: misc_feature
        (B) LOCATION: 6..15
        (D) OTHER INFORMATION:/standard_name= "dodecameric G-box
            element"

(ix) FEATURE:
        (A) NAME/KEY: misc_feature
        (B) LOCATION: 26..35
        (D) OTHER INFORMATION:/standard_name= "dodecameric G-box
            element"

(ix) FEATURE:
        (A) NAME/KEY: misc_feature
        (B) LOCATION: 76..85
        (D) OTHER INFORMATION:/standard_name= "dodecameric G-box
            element"

(ix) FEATURE:
        (A) NAME/KEY: misc_feature
        (B) LOCATION: 96..105
        (D) OTHER INFORMATION:/standard_name= "dodecameric G-box
            element"

(xi) SEQUENCE DESCRIPTION: SEQ ID NO:33:

GATCCTCCAC GTGGCTATTC AATACTCCAC GTGGCTGGCT CACCCCTCGA GCTGCAGTAG    60

CATGCTTCAG TCTGTTCCAC GTGGCTTCAA GATTTTCCAC GTGGC                   105

(2) INFORMATION FOR SEQ ID NO:34:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (ix) FEATURE:
        (A) NAME/KEY: misc_feature
        (B) LOCATION: 5..14
        (D) OTHER INFORMATION:/standard_name= "dodecameric G-box
            element"

(ix) FEATURE:
        (A) NAME/KEY: misc_feature
        (B) LOCATION: 25..34
        (D) OTHER INFORMATION:/standard_name= "Dodecameric G-box
            element"
```

```
        (ix) FEATURE:
              (A) NAME/KEY:  misc_feature
              (B) LOCATION:  75..84
              (D) OTHER INFORMATION:/standard_name= "dodecameric G-box
                  element"

(ix) FEATURE:
              (A) NAME/KEY:  misc_feature
              (B) LOCATION:  95..104
              (D) OTHER INFORMATION:/standard_name= "dodecameric G-box
                  element"

(xi) SEQUENCE DESCRIPTION:  SEQ ID NO:34:

GATCGCCACG TGGAAAATCT TGAAGCCACG TGGAACAGAC TGAAGCATGC TACTGCAGCT      60

CGAGGGGTGA GCCAGCCACG TGGAGTATTG AATAGCCACG TGGAG                    105

(2) INFORMATION FOR SEQ ID NO:35:

(i) SEQUENCE CHARACTERISTICS:
              (A) LENGTH:  149 base pairs
              (B) TYPE:  nucleic acid
              (C) STRANDEDNESS:  single
              (D) TOPOLOGY:  linear (ii) MOLECULE TYPE:  other nucleic acid
              (A) DESCRIPTION:  /desc = "oligonucleotide"

(iii) HYPOTHETICAL:  NO (ix) FEATURE:
              (A) NAME/KEY:  misc_feature
              (B) LOCATION:  13..50
              (D) OTHER INFORMATION:/standard_name= "CHS Unit I
                  regulatory element"

(ix) FEATURE:
              (A) NAME/KEY:  misc_feature
              (B) LOCATION:  105..142
              (D) OTHER INFORMATION:/standard_name= "CHS Unit I
                  regulatory element"

(xi) SEQUENCE DESCRIPTION:  SEQ ID NO:35:

GATCCCCTTA TTCCACGTGG CCATCCGGTG GCCGTCCCTC CAACCTAACC TCCCTTGTGG      60

CTCACCCCTC GAGCTGCAGT AGCATGCTTC AGTCTGTCCT TATTCCACGT GGCCATCCGG    120

TGGCCGTCCC TCCAACCTAA CCTCCCTTG                                      149

(2) INFORMATION FOR SEQ ID NO:36:

(i) SEQUENCE CHARACTERISTICS:
              (A) LENGTH:  149 base pairs
              (B) TYPE:  nucleic acid
              (C) STRANDEDNESS:  single
              (D) TOPOLOGY:  linear (ii) MOLECULE TYPE:  other nucleic acid
              (A) DESCRIPTION:  /desc = "oligonucleotide"

(iii) HYPOTHETICAL:  NO (ix) FEATURE:
              (A) NAME/KEY:  misc_feature
              (B) LOCATION:  12..49
              (D) OTHER INFORMATION:/standard_name= "CHS Unit I
                  regulatory element"

(ix) FEATURE:
              (A) NAME/KEY:  misc_feature
              (B) LOCATION:  104..141
              (D) OTHER INFORMATION:/standard_name= "CHS Unit I
                  regulatory element"

(xi) SEQUENCE DESCRIPTION:  SEQ ID NO:36:
```

-continued

```
GATCCAAGGG AGGTTAGGTT GGAGGGACGG CCACCGGATG GCCACGTGGA ATAAGGACAG      60

ACTGAAGCAT GCATCTGCAG CTCGAGGGGT GAGCCACAAG GGAGGTTAGG TTGGAGGGAC     120

GGCCACCGGA TGGCCACGTG GAATAAGGG                                       49
```

SPECIFIC GENE ACTIVATION BY CHIMERIC GAL4 TRANSCRIPTION FACTORS IN STABLE TRANSGENIC PLANTS

FIELD OF THE INVENTION

The present invention pertains to a method of regulating transgene expression using a two component system and, more particularly, to a system specific for stably transformed plants which comprises 1) a promoter containing Gal4 binding sites and, optionally, additional regulatory elements and 2) a chimeric transcription factor containing a Gal4 DNA binding domain and an activation domain.

BACKGROUND OF THE INVENTION

Improvement of crop plants for a variety of traits, including disease and pest resistance, and grain quality improvements such as oil, starch or protein composition, can be achieved by introducing new or modified genes (transgenes) into the plant genome. Expression of genes, including transgenes, is in general controlled by the promoter through a complex set of protein/DNA and protein/protein interactions. Promoters can impart patterns of expression that are either constitutive or limited to specific tissues or times during development. There are limitations in the types of expression achievable using existing promoters for transgene expression. One limitation is in the expression level achievable. It is difficult to obtain traits that require relatively high expression of an introduced gene, due to limitations in promoter strength. A second limitation is that the pattern of expression conferred by the particular promoter employed is inflexible in that the same promoter-dependent pattern of expression is conferred from generation to generation.

For imparting certain traits, it is desirable to have the ability to regulate the trait-conferring transgene expression differently in successive generations. One example would be a trait that has a side effect of being detrimental to seed viability, but which is desired in a grain product. For example, one can envision using plant seeds to produce proteins, starches, or other substances in grain (product seeds not used for further planting) which are detrimental to seed viability. In this case it would be desirable to carry the trait-conferring transgene in an inactive state in breeding lines up until the time of grain production. Then a new type of expression system is required to activate the trait gene in the grain.

Another limitation in the current methods of transgene expression is an inability to coordinately regulate multiple transgenes in transgenic crops. Multiple copies of the same promoter, directing coordinate regulation of multiple genes, can lead to gene inactivation through repeat induced gene silencing (Ye and Signer, 1996, Proc. National Acad. Sci. 93:10881–10886) or other means of cosuppression. Thus, a means of coordinately regulating multiple transgenes is desirable.

Transcriptional activation is primarily mediated through transcription factors that interact with enhancer and promoter elements. Binding of transcription factors to such DNA elements constitutes a crucial step in transcriptional initiation. Structural and finctional analyses of transcription factors revealed that many of these proteins have a modular protein structure, i.e., they are often modular, made up of a specific DNA-binding domain and a separate and independently acting activation domain. Researchers have found that heterogeneous domains can be combined, the resultant composite activators being functional in mammalian cells. An example of such an activator is the protein produced by fusion of the Gal4 DNA-binding domain with the activation domain of VP16.

Each transcription factor binds to its specific binding sequence in a promoter and activates expression of the linked coding region through interactions with coactivators and/or proteins that are a part of the transcription complex. A DNA binding domain and an activation domain derived from different proteins can be linked to produce a chimeric transcription factor. One transcription factor that has been studied is the yeast transcription factor Gal4 which is composed of a DNA binding domain and an activation domain. Native Gal4, a protein of 881 amino acids, is a transcriptional activator of genes required for galactose catabolism in the yeast *S. cerevisiae*. The protein binds specifically to the upstream activating sequence called $UAS_G$ and activates transcription of the divergently transcribed genes GAL1 and GAL 10.

A two component transcription factor/target promoter system could be used to address the above limitations of transgene expression with existing promoters. For example, a chimeric transcription factor comprising the Gal4 DNA binding domain could be used as the basis of a two component gene expression system. In fact, chimeric transcription factors containing the Gal4 DNA binding domain and various activation domains have been successfully used in plant cells in transient assays, but not in stable transformants.

The yeast Gal4 DNA binding domain fused to one or two of its own activation domains was able to activate expression of a chloramphenicol acetyl transferase (CAT) reporter gene, with Gal4 binding sites in the promoter, in a transient assay in tobacco protoplasts (Ma et al., 1988 Nature 334, p 631–633). The expression level was similar to that directed by the CaMV 35S promoter. A chimeric transcription factor composed of the Gal4 DNA binding domain and an *E. coli* DNA fragment-encoded activation domain also activated expression.

A chimeric transcription factor composed of the Gal4 DNA binding domain and the proline-rich activation domain of GBF1, a G-box binding transcription factor of *Arabidopsis thaliana* activated expression of a luciferase reporter gene with Gal4 binding sites in the promoter when tested in a transient assay using soybean cell culture protoplasts (Schindler et al., 1992 EMBO J 11 p 1275–1289). Activated expression was less than that conferred by the Gal4 /E. coli activation domain factor. No activation by the intact Gal4 protein was observed, which was speculated to be due to possible inefficient translation or protein instability.

A chimeric transcription factor composed of the Gal4 DNA binding domain and the activation domain of PvAlf, a seed-specific transcription factor of *Phaseolus vulgaris*, activated expression of a CAT reporter gene, with Gal4 binding sites in the promoter, in a transient assay in bean cotyledon cells (Bobb et al., 1995 Plant J 8 p 101–113).

No effect of the Gal4 DNA binding domain was detected in stably transformed tobacco plants containing GUS and NPTII reporter genes with Gal4 sites in their promoters (Reuchek et al., 1995 Plant Cell Reports 14 p 773–776). No expression of the Gal4 DNA binding domain protein was detected.

Canadian Patent Application Number 2,150,039, which was published on Aug. 9, 1996, describes a method to control the expression of genes in transgenic plants using native Gal4 as the transactivator. Specifically, it discloses an example in which a GUS reporter gene with Gal4 sites in its promoter is targeted by Gal4 protein expressed from the constitutive CaMV 35S promoter. These two components were co-introduced into Arabidopsis root cells and leaf tissue growing from callus cultures was assayed. When this leaf material was stained for GUS only the veins were positive for expression of the reporter activity. These results are inconsistent with the expectation of constitutive expression throughout the leaf and in all tissues. In other words, the expected result was that the expression of GUS should have been indistinguishable from the example of GUS expressed directly from the 35S promoter (Benfey et al., EMBO J 9:1685–1696 (1990); Odell et al., Nature 313: 810–812 (1985)). Thus, it is likely that the expression which was detected only in the veins is due not to the finctioning of the described system controlled by the 35S promoter. Expression in the veins may be due to integration of GUS adjacent to an endogenous regulatory sequence that directs expression in the veins (Sundaresan et al., 1995, Genes & Development 9:1797–1810; Topping et al., 1994 Plant J. 5:895–903), or to background expression from the promoter operably linked to the GUS coding region. There is no indication that the Gal4 transactivator is expressed and functioning to regulate GUS expression, since it is co-introduced and not added separately to activate the Gal4 site promoter. This result indicates the failure of the transactivation system with Gal4, as was found by other researchers, as discussed above.

While it is known that Gal4 chimeric transcription factor/target promoter systems can function in plant cells in transient assays, there are only reports of failed or inconclusive attempts to use this type of system in stably transformed plants. Thus, there is still a need for a two component system to regulate transgene expression. If such a system was available, then other techniques such as those described in PCT Application having International Publication Number WO 92/08341 which was published on May 29, 1992, the disclosure of which is hereby incorporated by reference, could be used to induce expression of the trait gene only in the production field. In other cases, a two-component system may be used to amplify the expression level from a promoter with desirable tissue or cell type specificity, while maintaining the desired tissue or cell type specificity. Also a two-component system may be used to coordinately regulate multiple transgenes. Still further, an expression system that achieves levels of expression not previously obtained with known promoters is desirable for traits wherein high levels of protein products are required to achieve the traits such as the expression of a protein having a high lysine and/or methionine content which in turn then can improve seed amino acid composition.

SUMMARY OF THE INVENTION

This invention concerns a method for regulating gene expression in a stably transformed transgenic plant cell which comprises combining into the genome of the plant cell:

a) a first chimeric gene comprising in the 5' to 3' direction:
(1) a promoter operably linked to at least one Gal4 binding sequence;
(2) a coding sequence or a complement thereof operably linked to the promoter; and
(3) a polyadenylation signal sequence operably linked to the coding sequence or a complement thereof; provided that when the promoter is a minimal promoter then the Gal4 binding sequence is located upstream of the minimal promoter; and b) a second chimeric gene comprising in the 5' to 3' direction:
(1) a promoter;
(2) a DNA sequence encoding a DNA binding domain of a Gal4 transcriptional activator;
(3) a DNA sequence encoding a transcriptional activation domain operably linked to the DNA sequence of (2); and
(4) a polyadenylation signal sequence operably linked to the DNA sequence of (3); wherein the expression of the second chimeric gene regulates expression of the first chimeric gene.

In another aspect, the first gene further can comprise at least one regulatory element.

BRIEF DESCRIPTION OF FIGURES AND SEQUENCES LISTINGS

Figure 4:
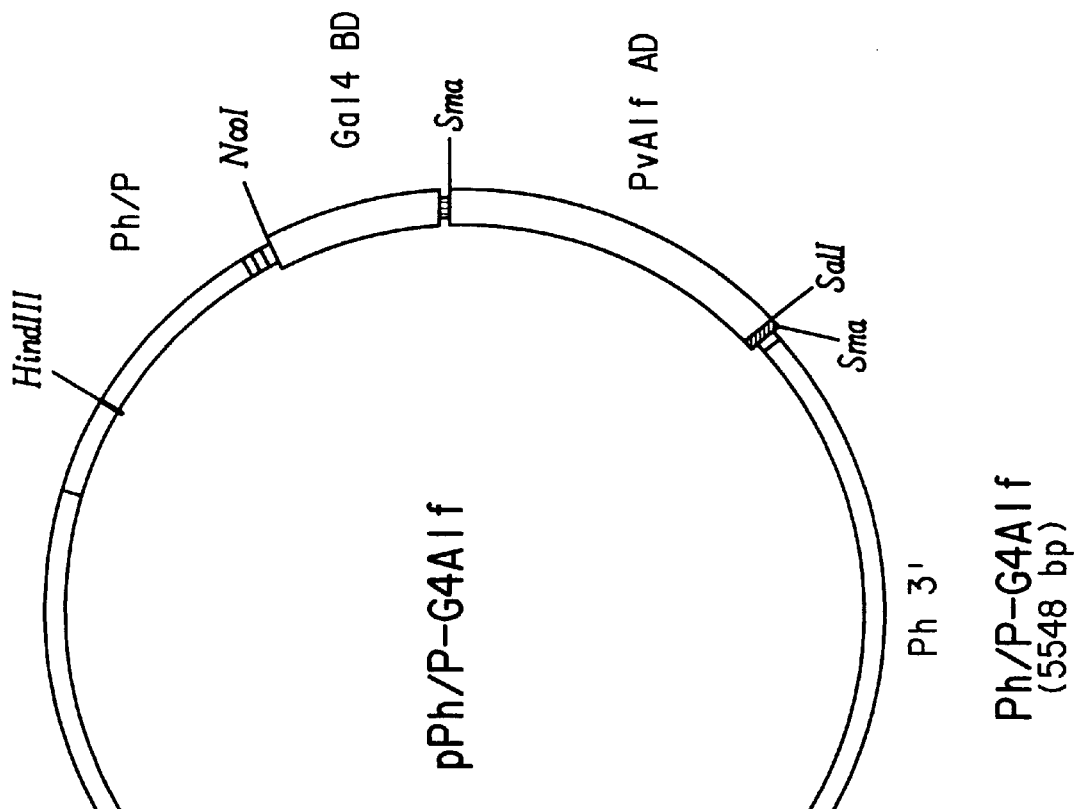

FIG. 4 is a map of plasmid pPh/P-G4Alf. This is plasmid pUC18 into which the chimeric Ph/P-Gal4 -PvAlf gene has been inserted. The chimeric gene consists of the phaseolin promoter and leader, the Gal4 DNA binding domain (BD), the PvAlf activation domain (AD), and the phaseolin 3' signal sequence region.

Figure 3:
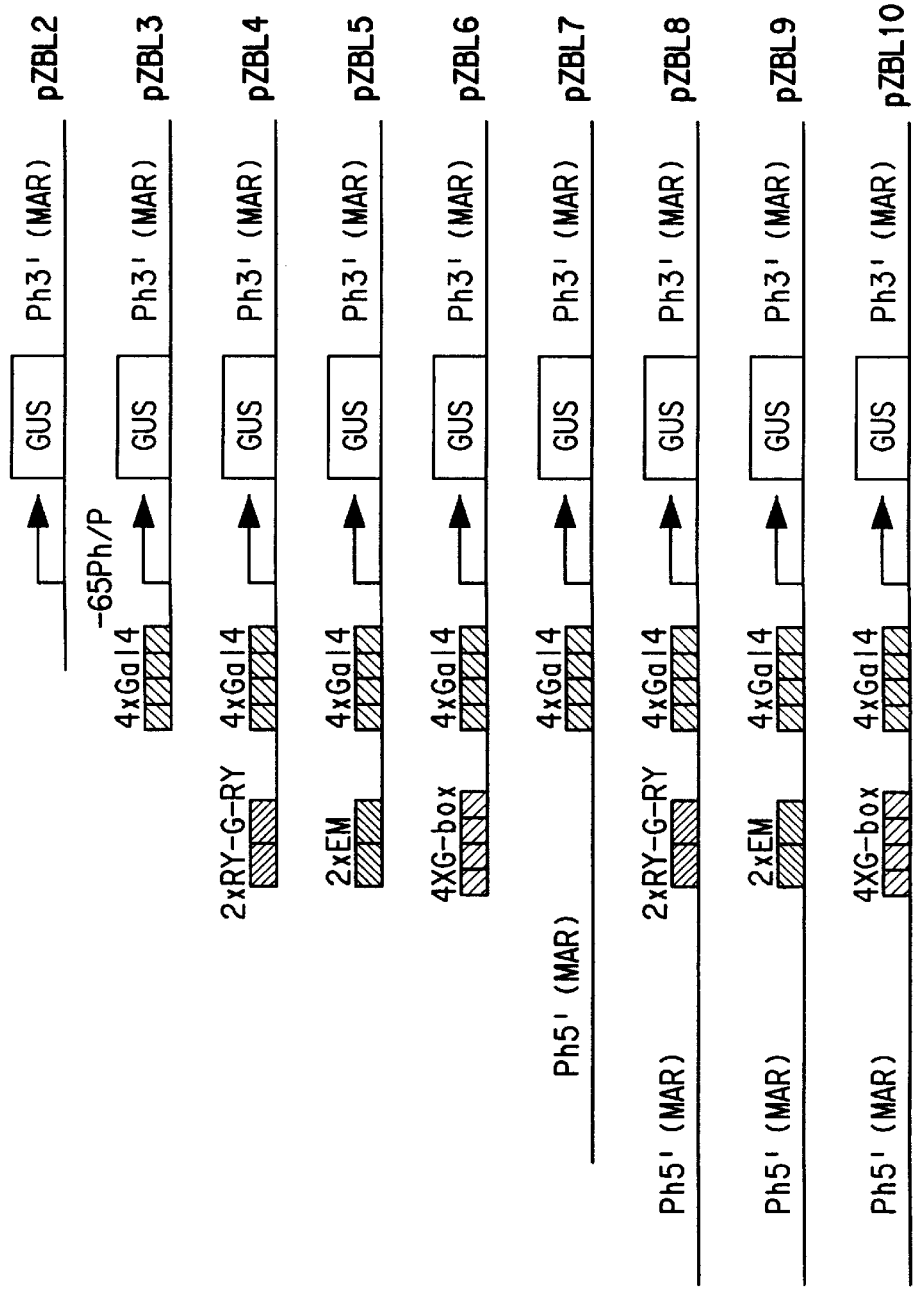
FIG. 3 is a diagram which compares the synthetic promoters used in the present study, and which represent combinations between Gal4 elements with other regulatory elements.
Figure 5:
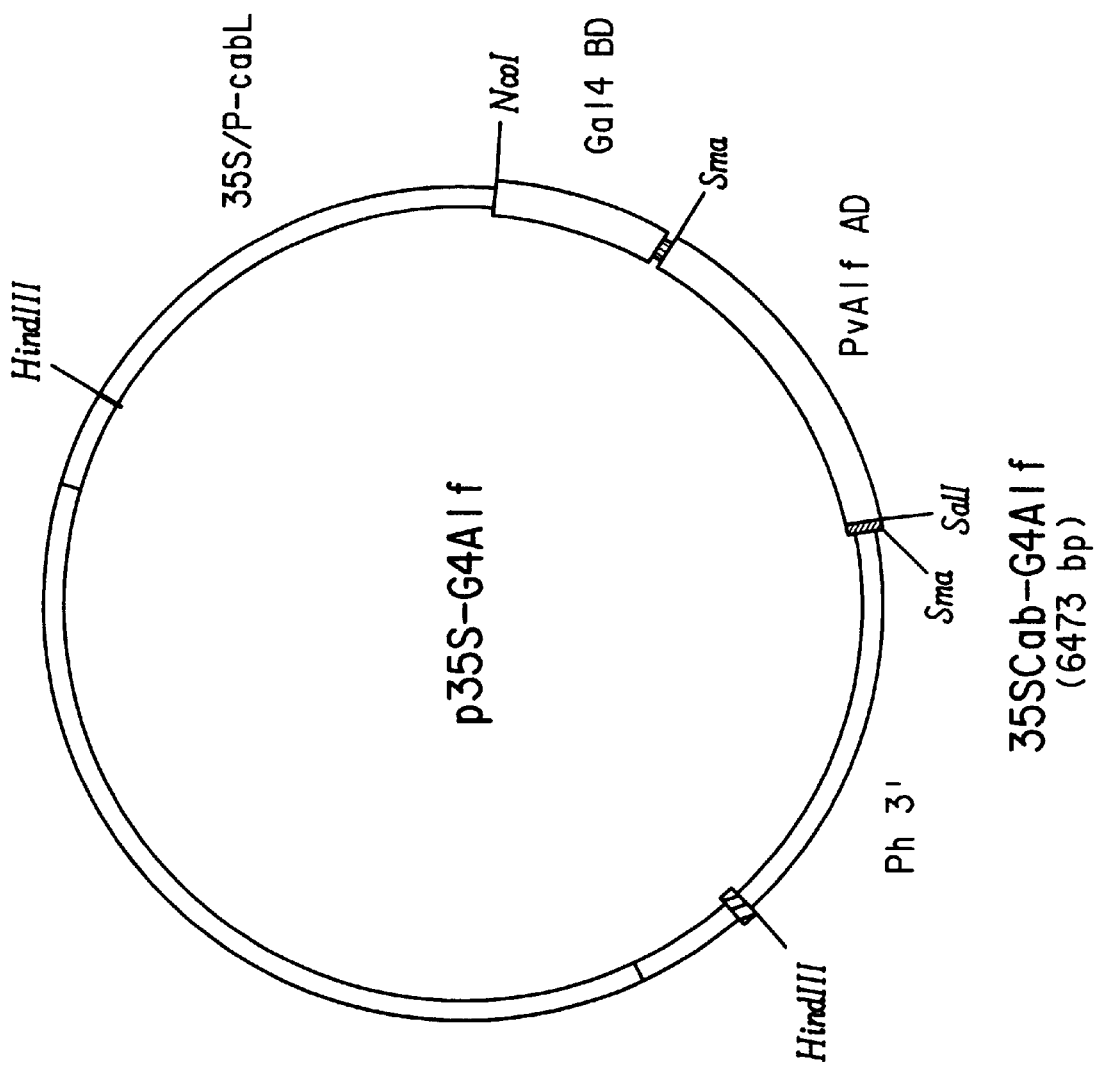

FIG. 5 is a map of plasmid p35S-G4Alf. This is plasmid pUC18 into which the chimeric p35S-Gal4 -PvAlf gene has been inserted. The chimeric gene is as that shown in FIG. 3 but with substitution of the 35S promoter and chlorophyll a/b binding protein leader for the phaseolin promoter.

Figure 6:
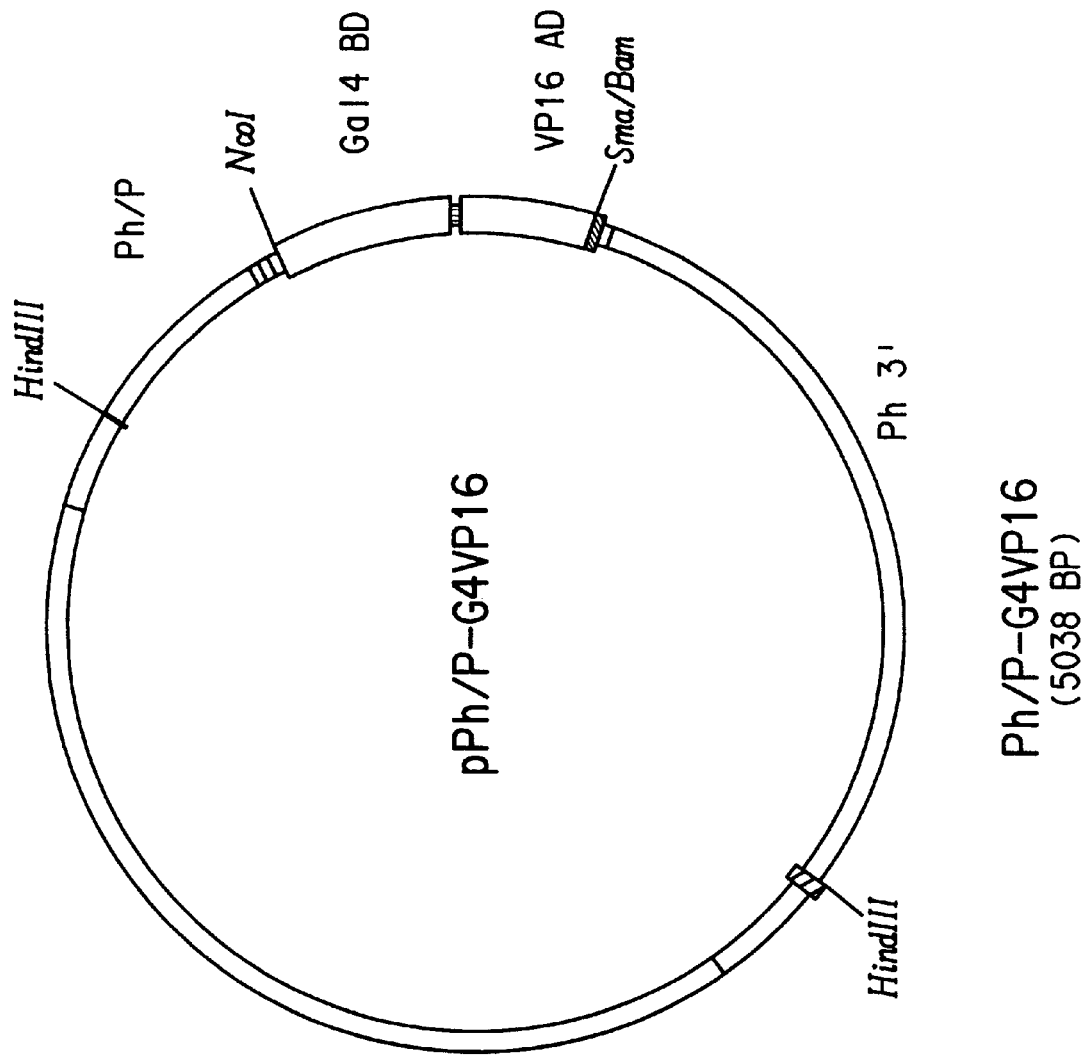

FIG. 6 is a map of pPh/P-G4VP16. This is plasmid pUC18 into which the chimeric Ph/P-Gal4 -VP16 gene has been inserted. The chimeric gene is as that shown in FIG. 3 but with substitution of the VP16 activation domain for the PvAlf activation domain.

Figure 7:
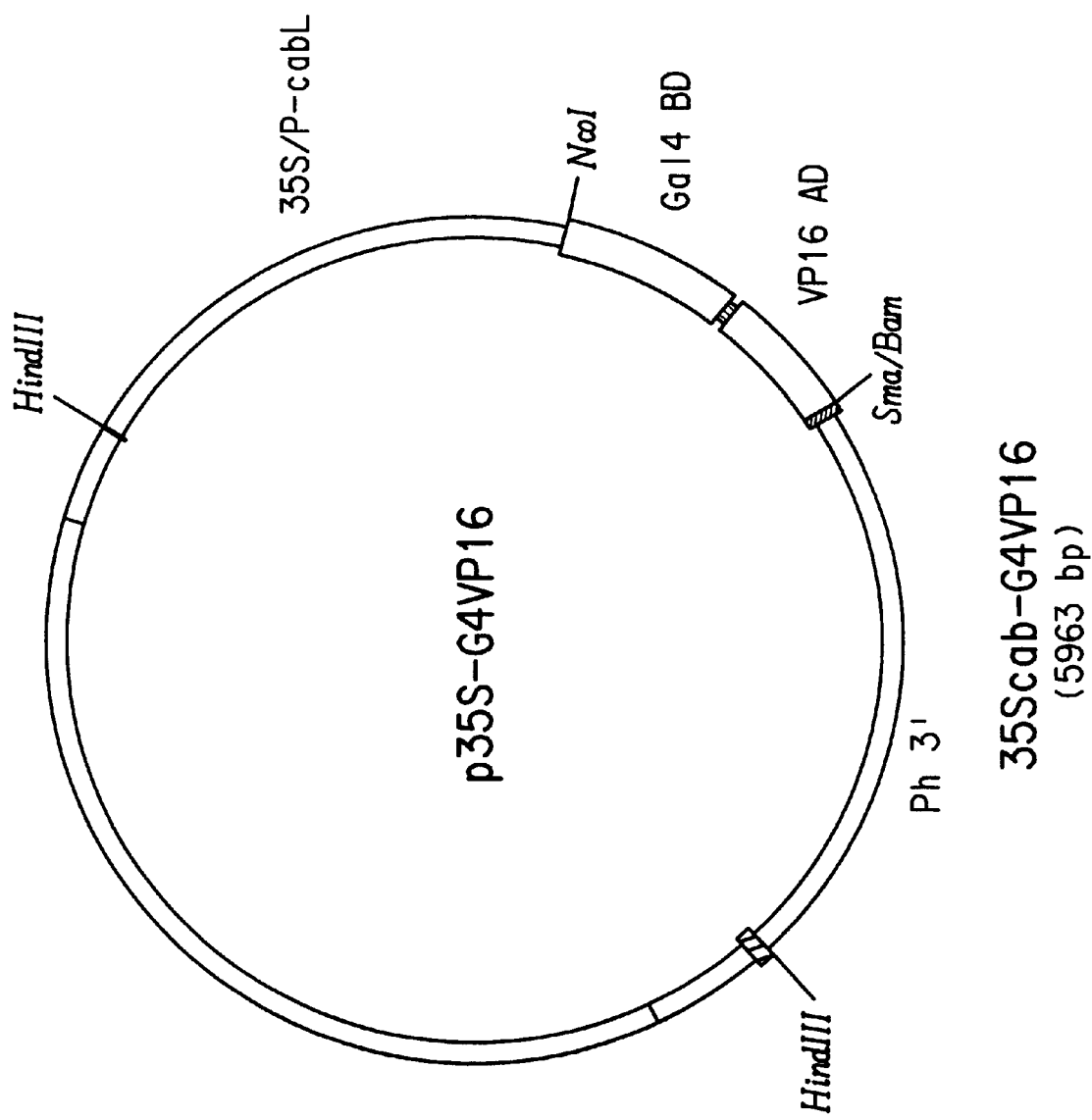

FIG. 7 is a map of plasmid p35S-G4VP16. This is plasmid pUC18 into which the chimeric p35S-Gal4 -VP16 gene has been inserted. The gene is as that shown in FIG. 4 but with substitution of the VP 16 activation domain for the PvAlf activation domain.

Figure 8:
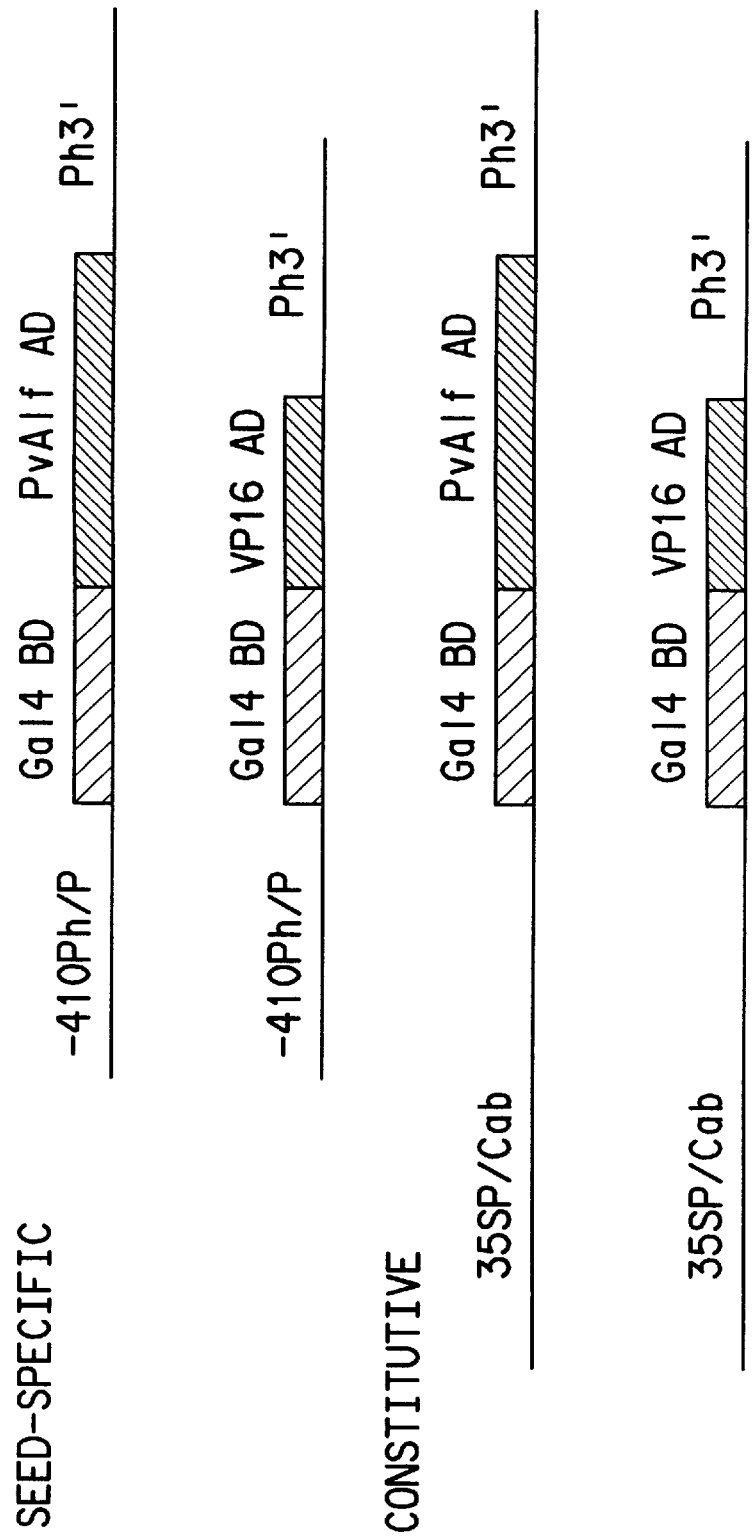

FIG. 8 depicts the different expression cassettes encoding chimeric Gal4 activators that are used in this work.

Figure 9:
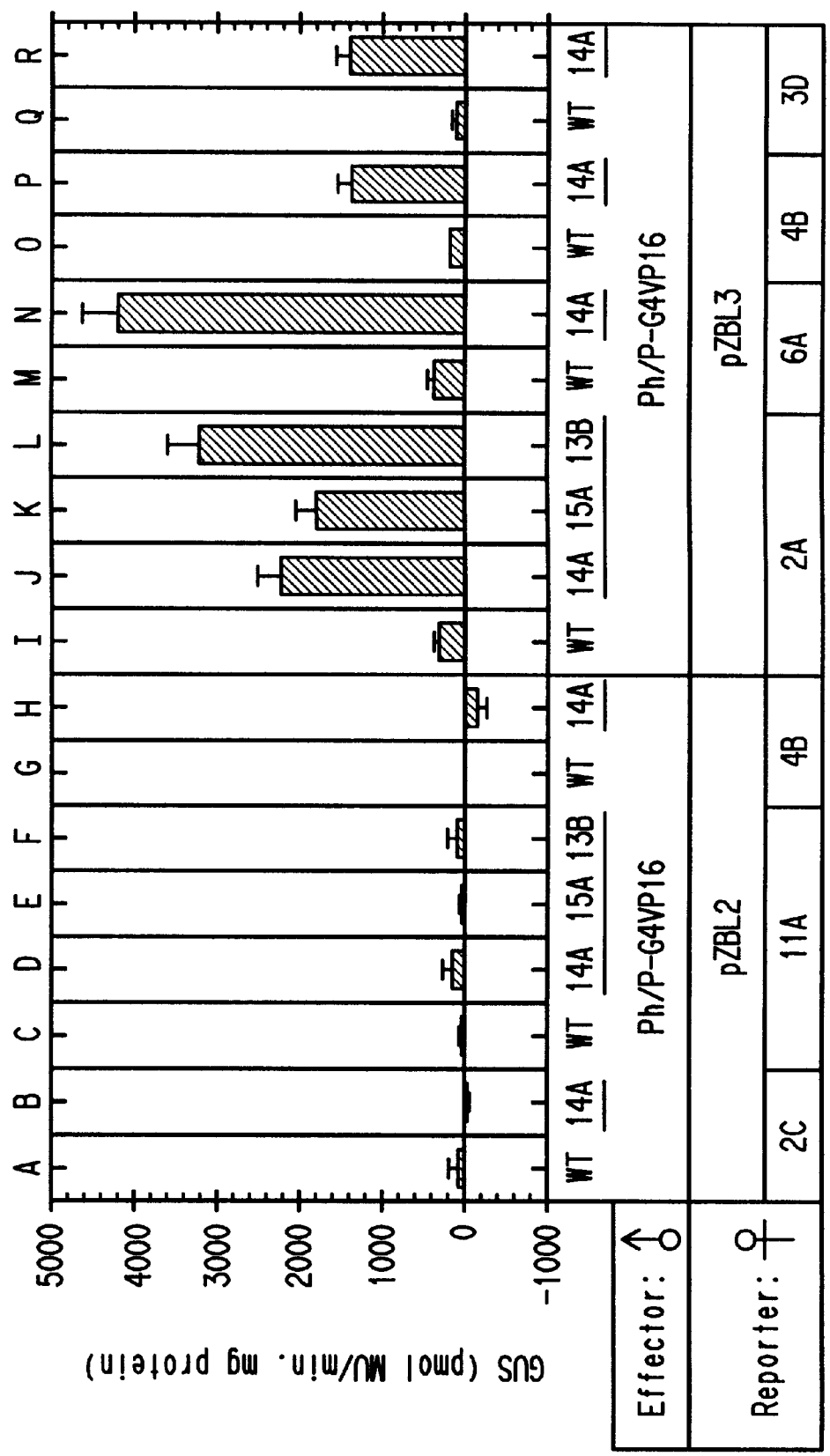

FIG. 9 presents the results of fluorometric assays demonstrating specific activation of the GUS reporter gene from pZBL3 by the chimeric transactivator Ph/P-G4VP16 in transgenic tobacco seeds. Genetic crosses were made between different reporter lines (pZBL2 2C, 11A, 4B; pZBL3 2A, 6A, 4B, 3D) and different Ph/P-G4VP16 effector lines (14A, 15A, and 13B).

Figure 10:
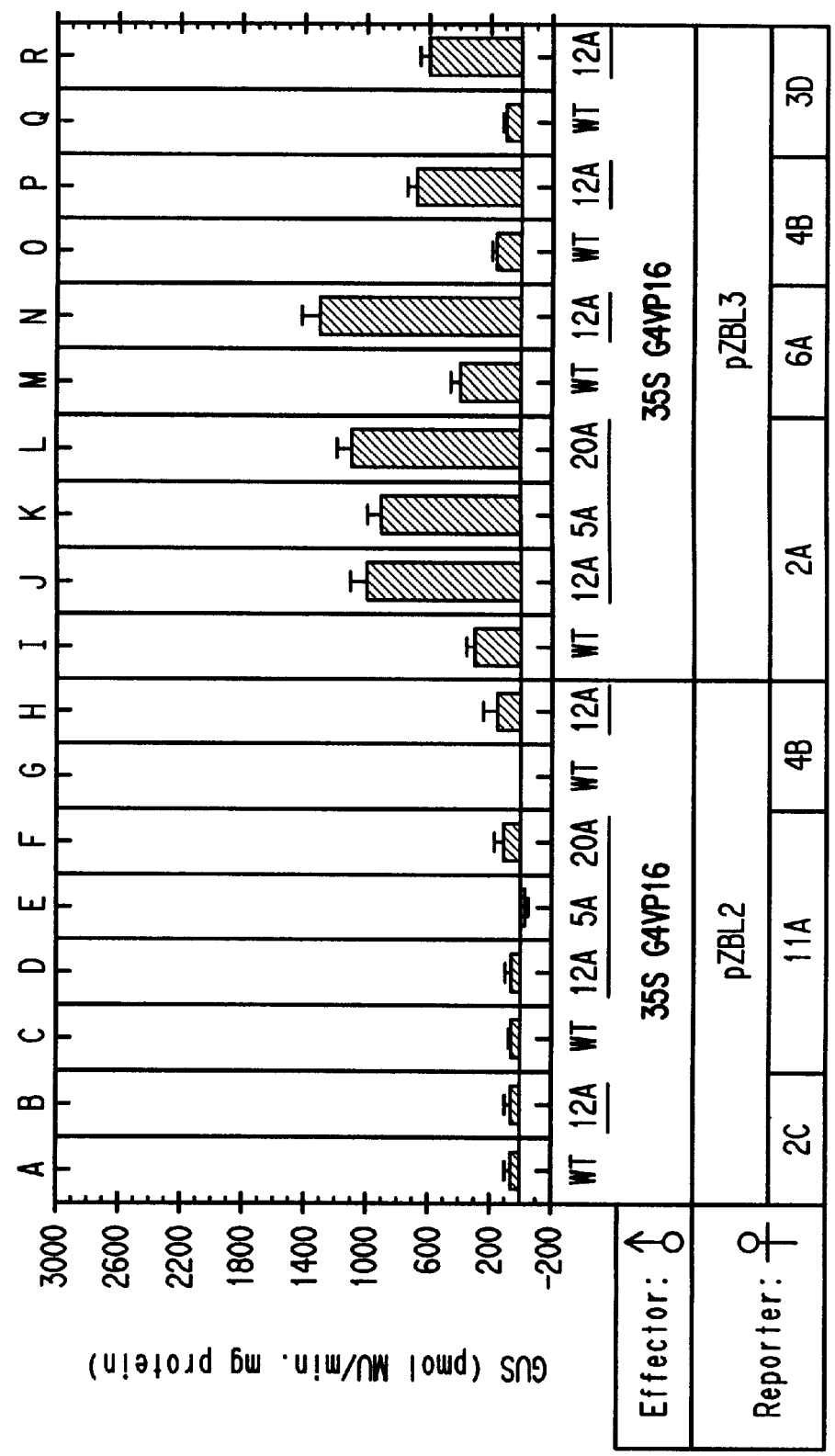

FIG. 10 presents the results of fluorometric assays demonstrating specific activation of the GUS reporter gene from pZBL3 by the chimeric transactivator 35S-G4VP16 in transgenic tobacco seeds. Genetic crosses were made between different reporter lines (pZBL2 2C, 11A, 4B; pZBL3 2A, 6A, 4B, 3D) and different 35S-G4VP16 effector lines (12A, 5A, and 20A).

Figure 11:
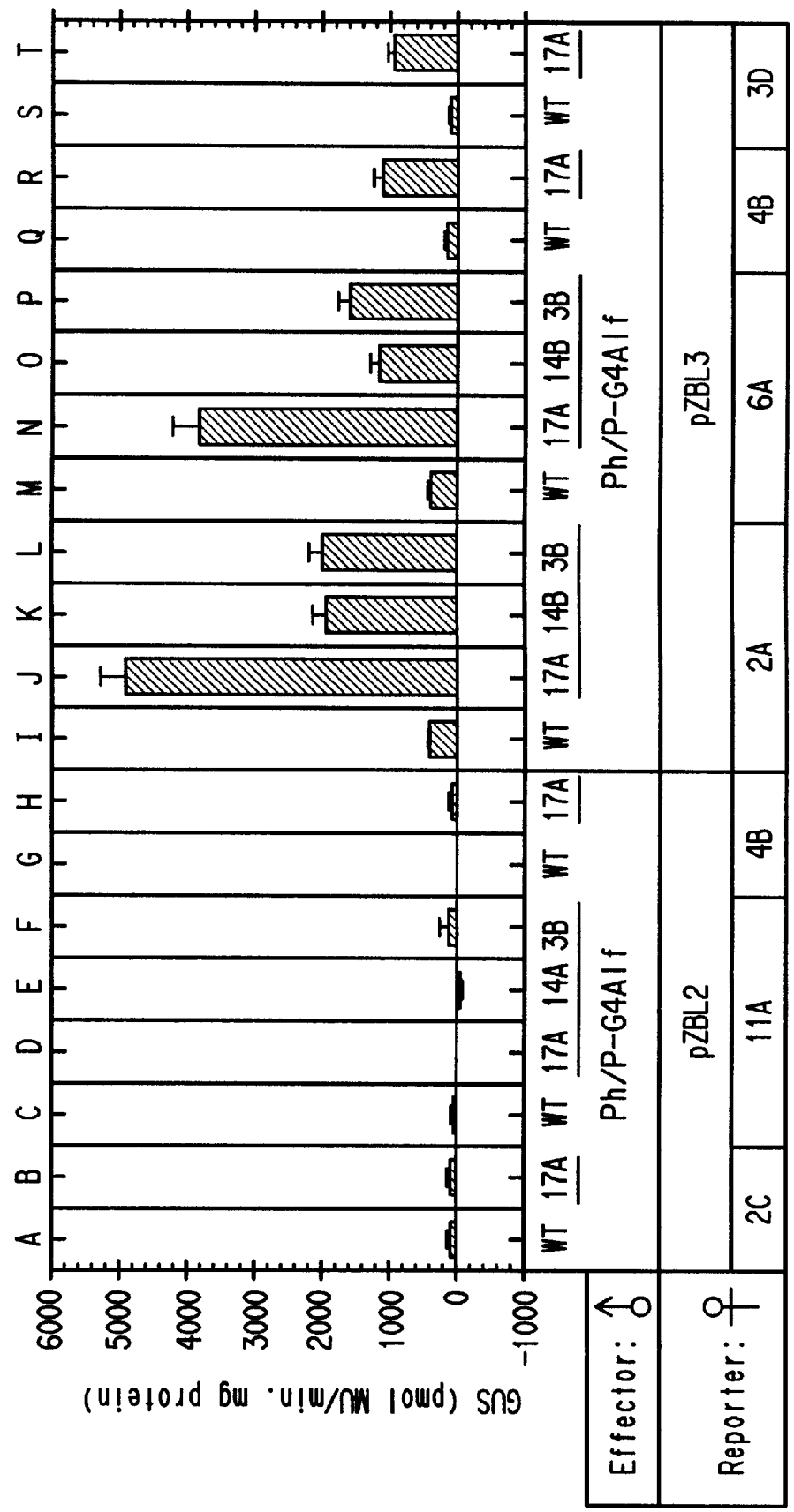

FIG. 11 presents the results of fluorometric assays demonstrating specific activation of the GUS reporter gene from pZBL3 by Ph/P-G4Alf in transgenic tobacco seeds. Genetic crosses were made between different reporter lines (pZBL2 2C, 11A, 4B; pZBL3 2A, 6A, 4B, 3D) and different Ph/P-G4Alf effector lines (17A, 14A, and 3B).

Figure 12:
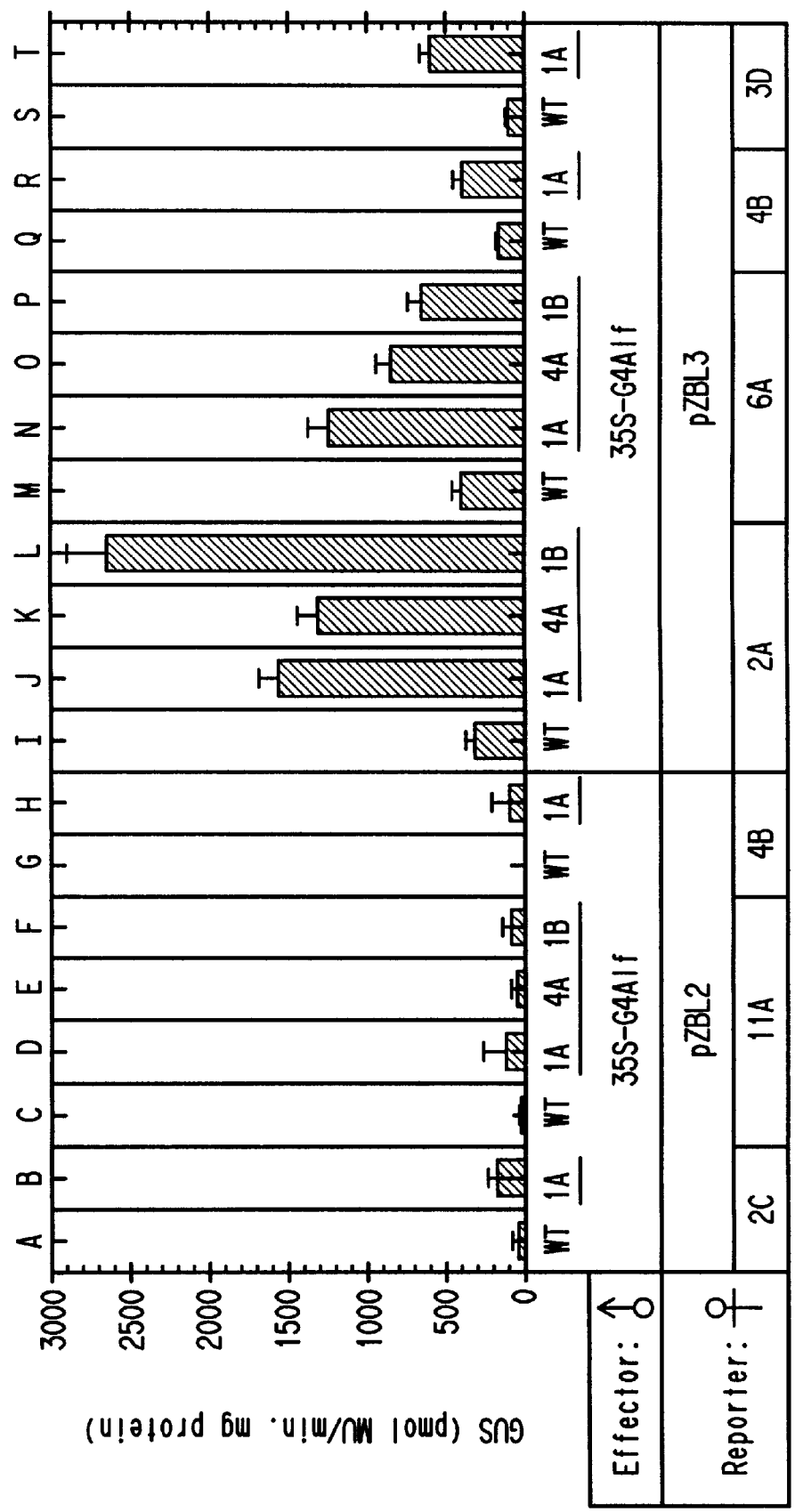

FIG. 12 presents the results of fluorometric assays demonstrating specific activation of the GUS reporter gene from pZBL3 by 35S-G4Alf in transgenic tobacco seeds. Genetic crosses were made between different reporter lines (pZBL2 2C, 11A, 4B; pZBL3 2A, 6A, 4B, 3D) and different 35S-G4Alf effector lines (1A, 4A, and 1B).

Figure 13:
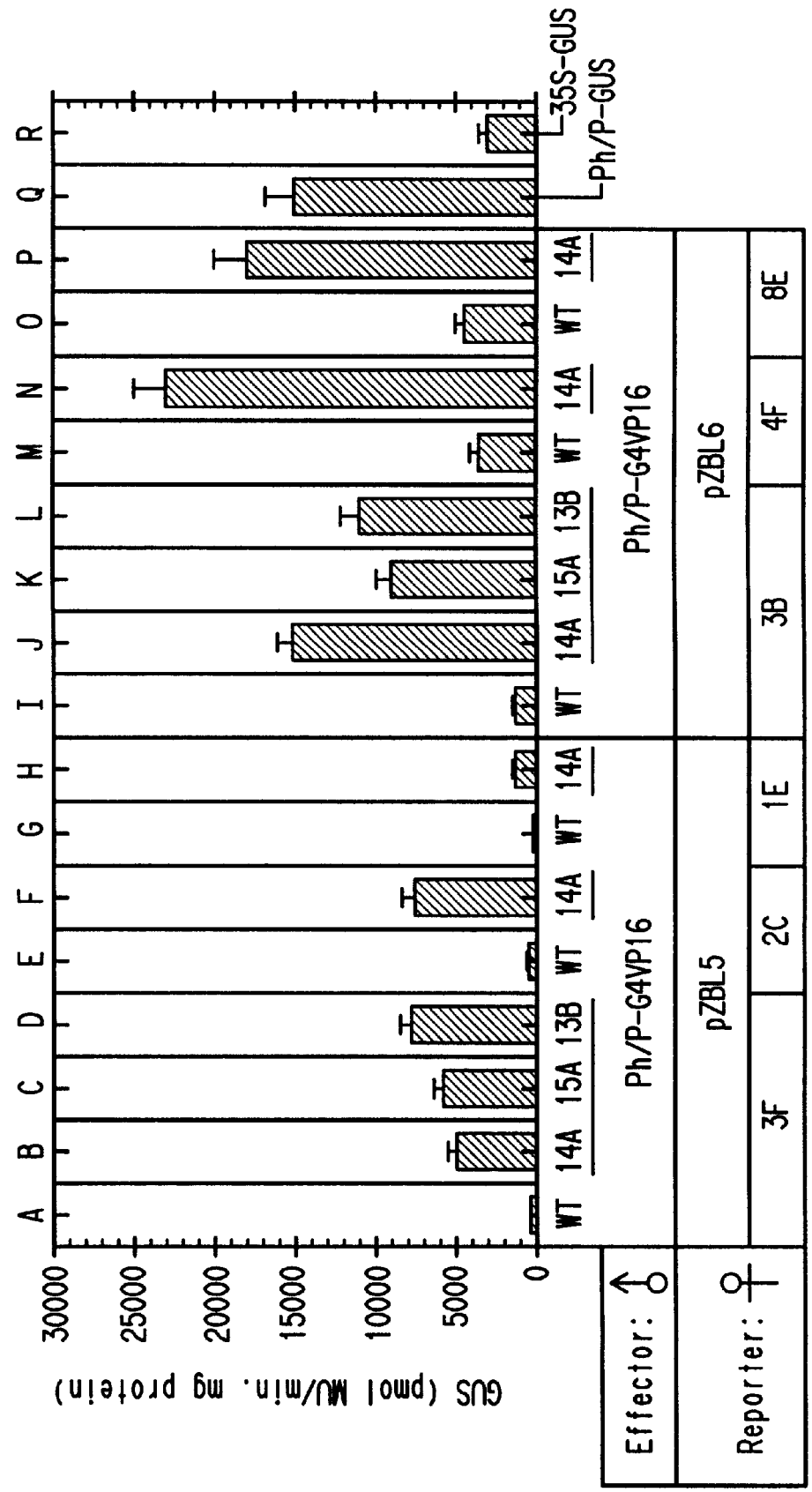

FIG. 13 presents the results of fluorometric assays demonstrating specific activation of the GUS reporter genes from pZBL5 and pZBL6 by Ph/P-G4VP16 in transgenic tobacco seeds. Genetic crosses were made between different reporter lines (pZBL5 3F, 2C, 1E; pZBL6 3B, 4F, 8E) and different Ph/P-G4VP16 effector lines (14A, 15A, and 13B). One highly expressed transgenic line containing −410Ph/P-GUS was used as a control, giving a high level of seed-specific expression. One highly expressed transgenic line of 35S-GUS was also used as a control.

Figure 14:
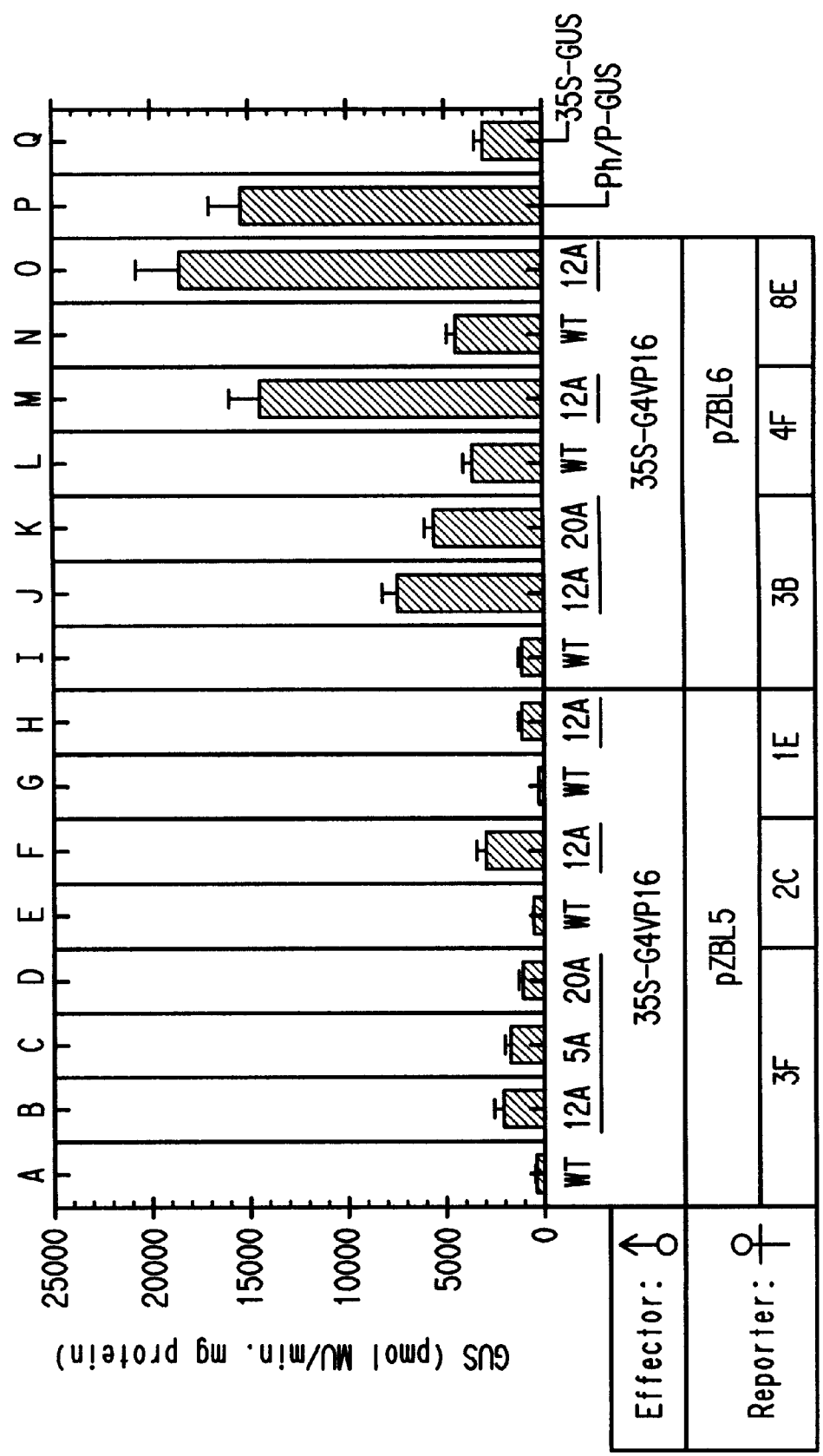

FIG. 14 presents the results of fluorometric assays demonstrating specific activation of the GUS reporter genes from pZBL5 and pZBL6 by 35S-G4VP16 in transgenic tobacco seeds. Genetic crosses were made between different reporter lines (pZBL5 3F, 2C, 1E; pZBL6 3B, 4F, 8E) and different 35S-G4VP16 effector lines (12A, 5A, and 20A). One highly expressed transgenic line containing −410Ph/P-GUS was used as a control, giving a high level of seed-specific expression. One highly expressed transgenic line of 35S-GUS was also used as a control.

Figure 15:
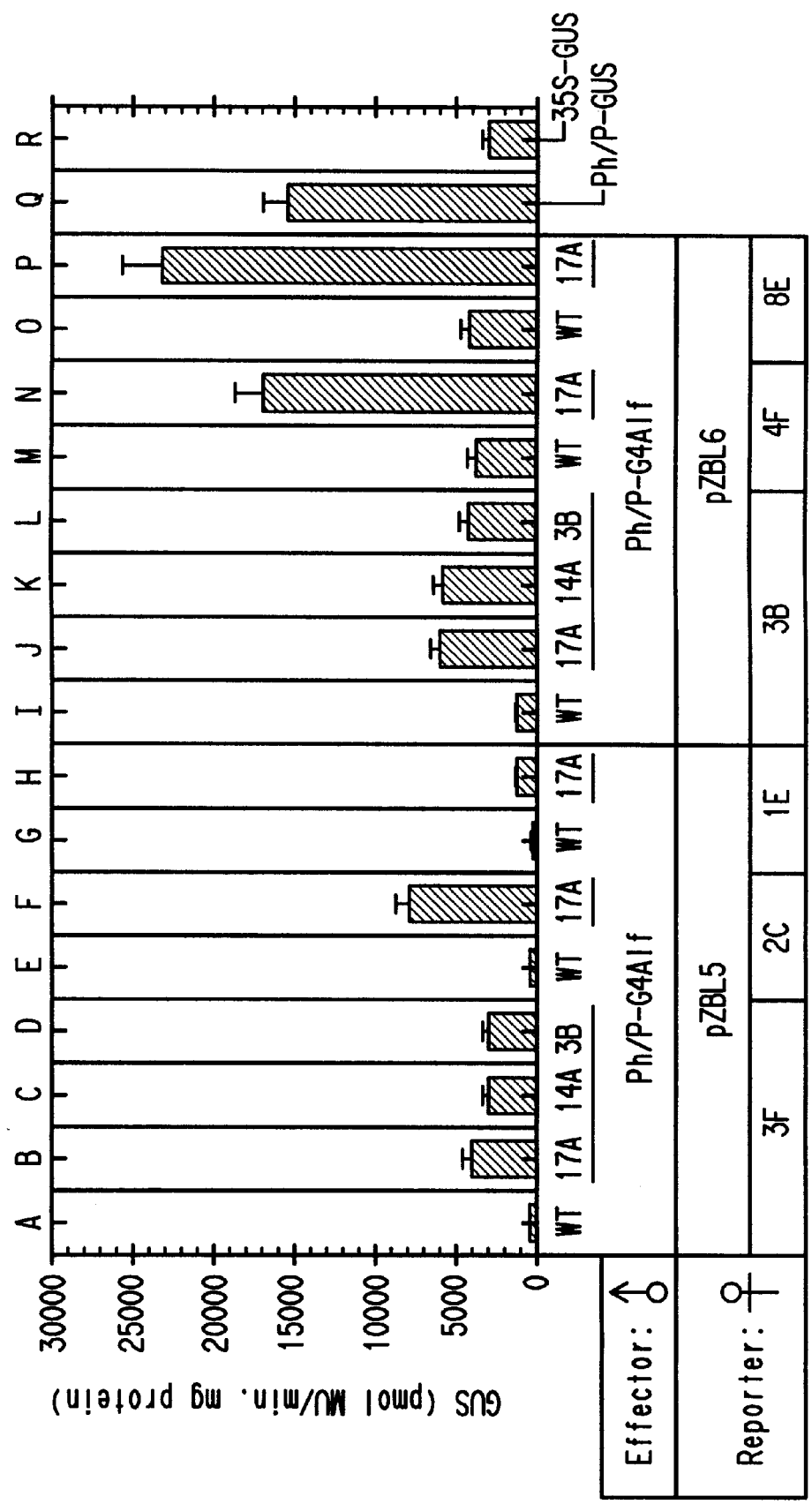

FIG. 15 presents the results of fluorometric assays demonstrating specific activation of the GUS reporter genes from pZBL5 and pZBL6 by Ph/P-G4Alf in transgenic tobacco seeds. Genetic crosses were made between different reporter lines (pZBL5 3F, 2C, 1E; pZBL6 3B, 4F, 8E) and different Ph/P-G4Alf effector lines (17A, 14A and 3B). One highly expressed transgenic line containing −410Ph/P-GUS was used as a control, giving a high level of seed-specific expression. One highly expressed transgenic line of 35S-GUS was also used as a control.

Figure 16:
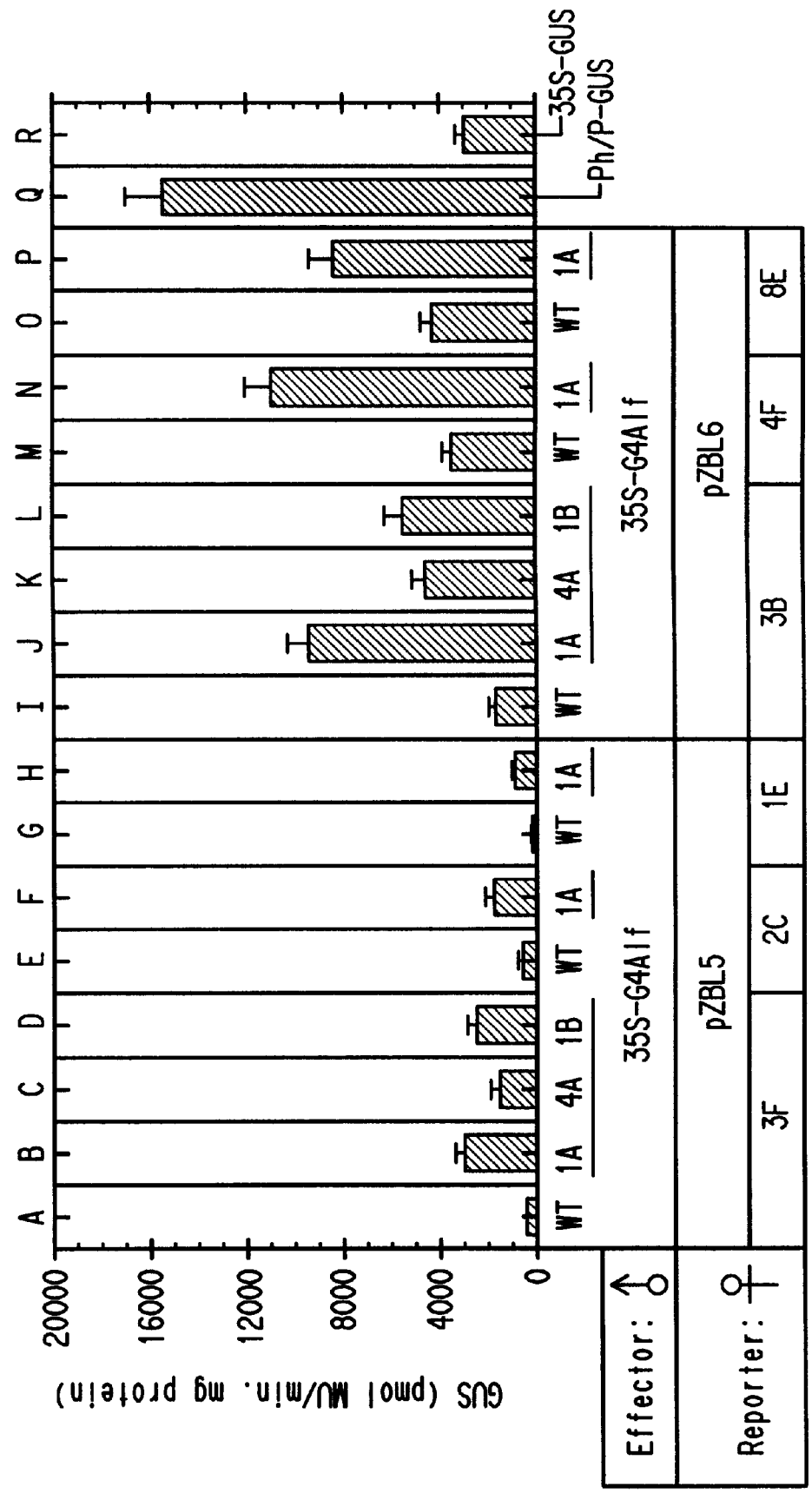

FIG. 16 presents the results of fluorometric assays demonstrating specific activation of the GUS reporter genes from pZBL5 and pZBL6 by 35S-G4Alf in transgenic tobacco seeds. Genetic crosses were made between different reporter lines (pZBL5 3F, 2C, 1E; pZBL6 3B, 4F, 8E) and different 35S-G4Alf effector lines (1A, 4A and 1B). One highly expressed transgenic line containing −410Ph/P-GUS was used as a control, giving a high level of seed-specific expression. One highly expressed transgenic line of 35S-GUS was also used as a control.

Figure 17:
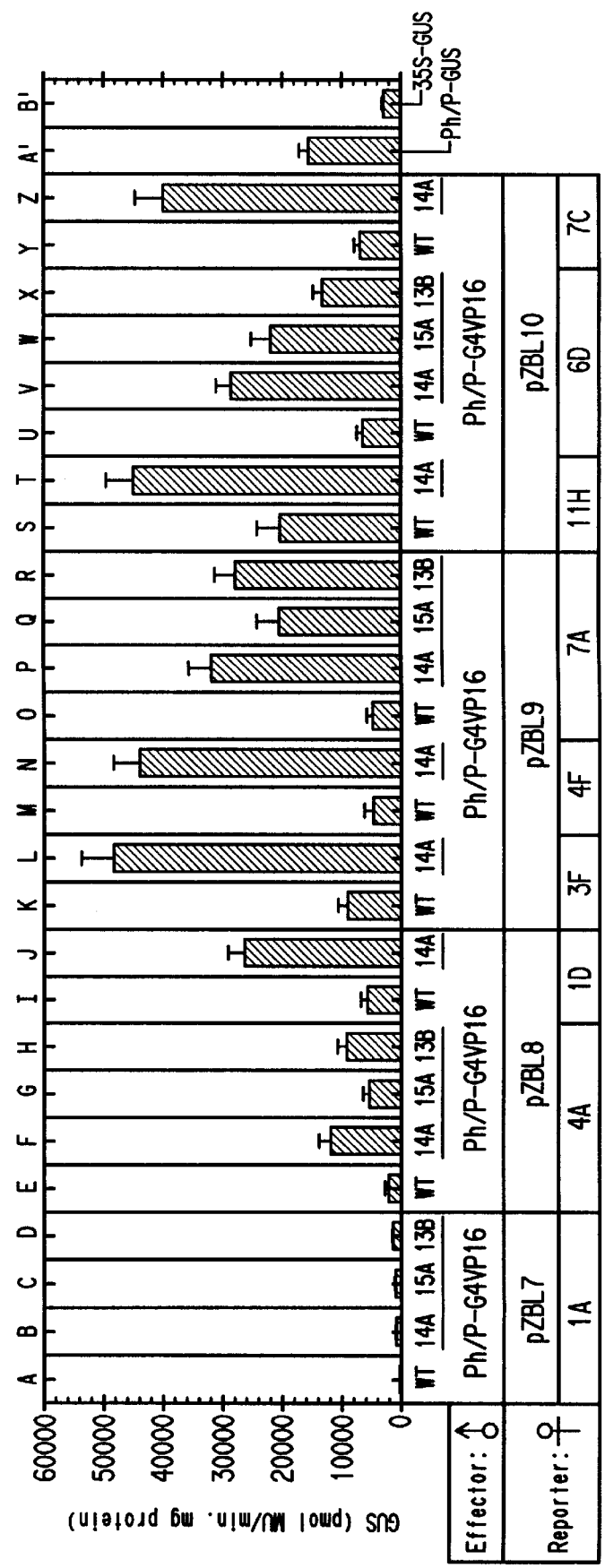

FIG. 17 presents the results of fluorometric assays demonstrating specific activation of the GUS reporter genes from pZBL7, pZBL8, pZBL9 and pZBL10 by Ph/P-G4VP16 in transgenic tobacco seeds. Genetic crosses were made between different reporter lines (pZBL7 1A; pZBL8 4A, 1D; pZBL9 3F, 4F, 7A; and pZBL10 11H, 6D, 7C) and different Ph/P-G4VP16 effector lines (14A, 15A, and 13B). One highly expressed transgenic line containing −410Ph/P-GUS was used as a control, giving a high level of seed-specific expression. One highly expressed transgenic line of 35S-GUS was also used as a control.

Figure 18:
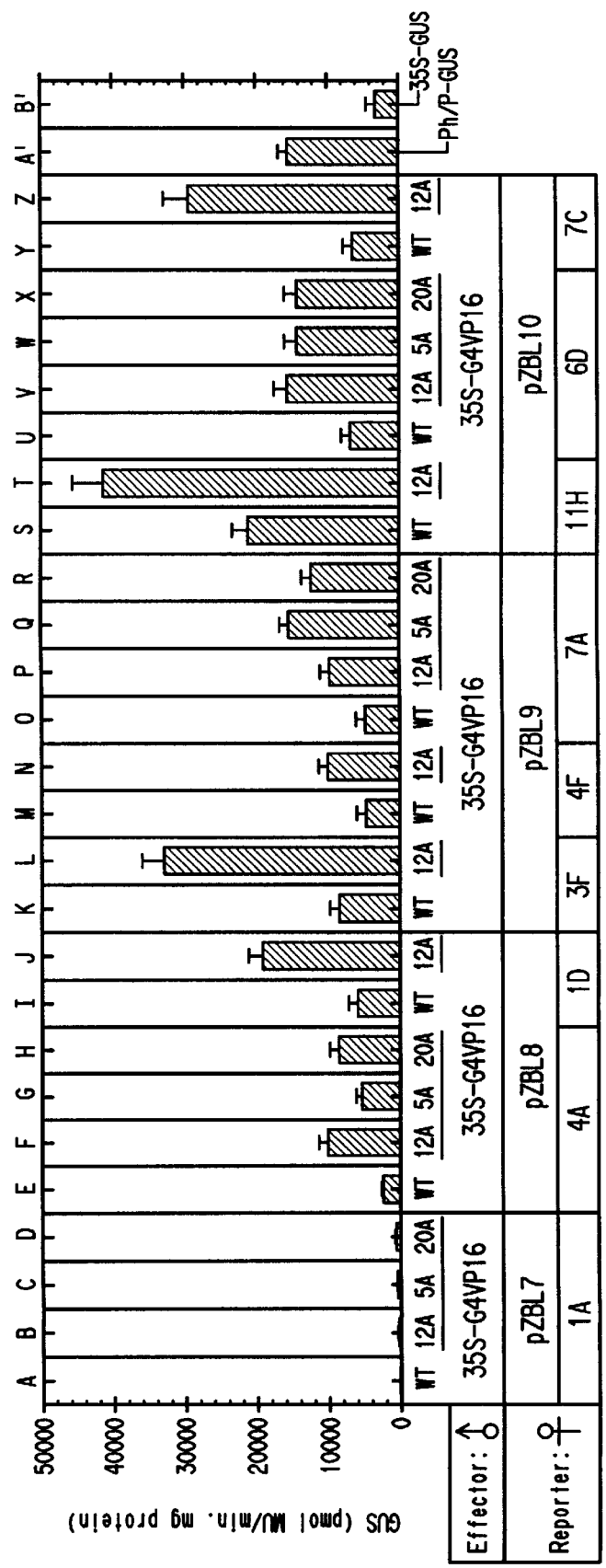

FIG. 18 presents the results of fluorometric assays demonstrating specific activation of the GUS reporter genes from pZBL7, pZBL8, pZBL9 and pZBL10 by 35S-G4VP16 in transgenic tobacco seeds. Genetic crosses were made between different reporter lines (pZBL7 1A; pZBL8 4A, 1D; pZBL9 3F, 4F, 7A; and pZBL10 11H, 6D, 7C) and different 35S-G4VP16 effector lines (12A, 5A, and 20A). One highly expressed transgenic line containing −410Ph/P-GUS was used as a control, giving a high level of seed-specific expression. One highly expressed transgenic line of 35S-GUS was also used as a control.

Figure 19:
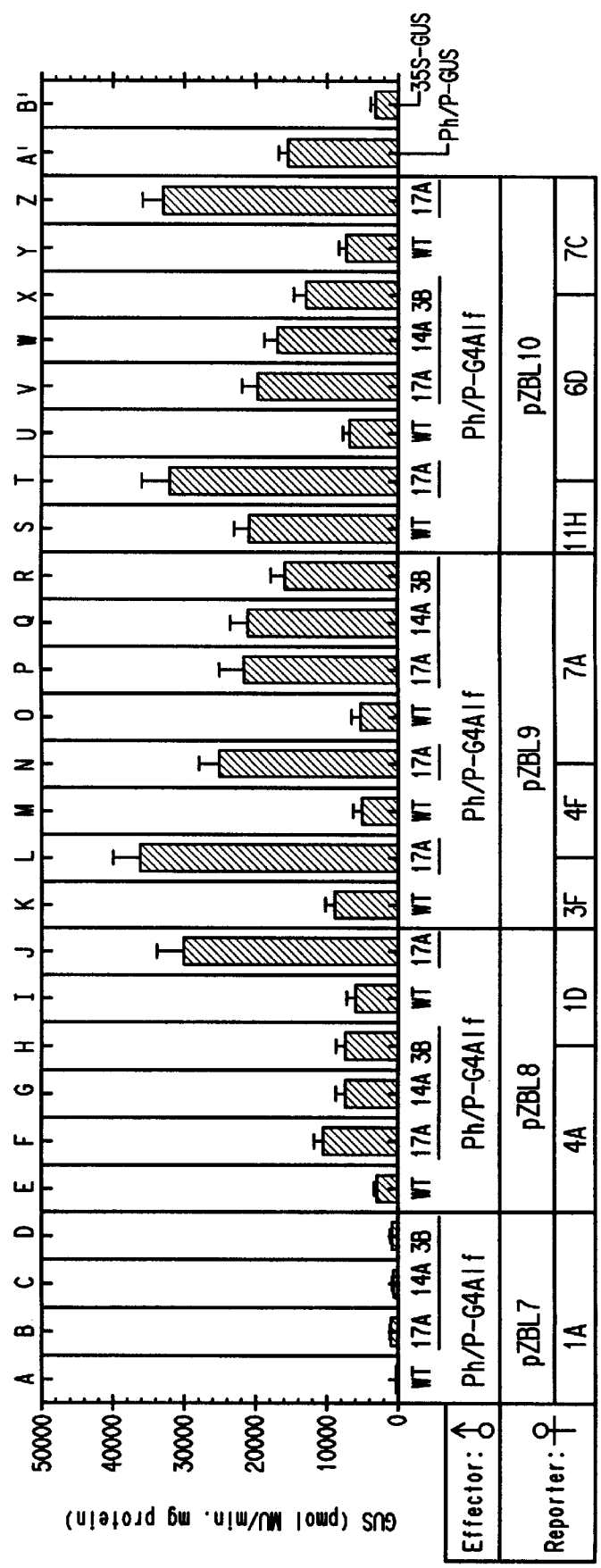

FIG. 19 presents the results of fluorometric assays demonstrating specific activation of the GUS reporter genes from pZBL7, pZBL8, pZBL9 and pZBL10 by Ph/P-G4Alf in transgenic tobacco seeds. Genetic crosses were made between different reporter lines (pZBL7 1A; pZBL8 4A, 1D; pZBL9 3F, 4F, 7A; and pZBL10 11H, 6D, 7C) and different Ph/P-G4Alf effector lines (17A, 14A, and 3B). One highly expressed transgenic line containing −410Ph/P-GUS was used as a control, giving a high level of seed-specific expression. One highly expressed transgenic line of 35S-GUS was also used as a control.

Figure 20:
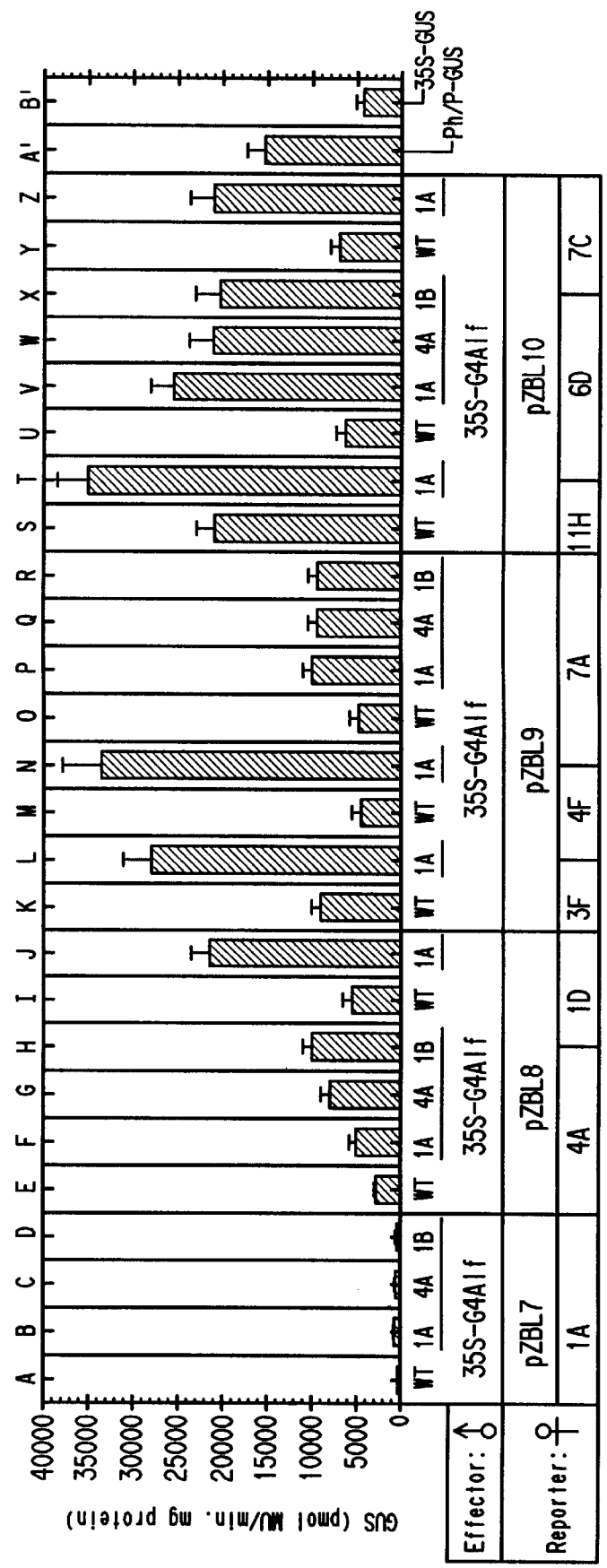

FIG. 20 presents the results of fluorometric assays demonstrating specific activation of the GUS reporter genes from pZBL7, pZBL8, pZBL9 and pZBL10 by 35S-G4Alf in transgenic tobacco seeds. Genetic crosses were made between different reporter lines (pZBL7 1A; pZBL8 4A, 1D; pZBL9 3F, 4F, 7A; and pZBL10 11H, 6D, 7C) and different 35S-G4Alf effector lines (1A, 4A, and 1B). One highly expressed transgenic line containing −410Ph/P-GUS was used as a control, giving a high level of seed-specific expression. One highly expressed transgenic line of 35S-GUS was also used as a control.

Figure 21:
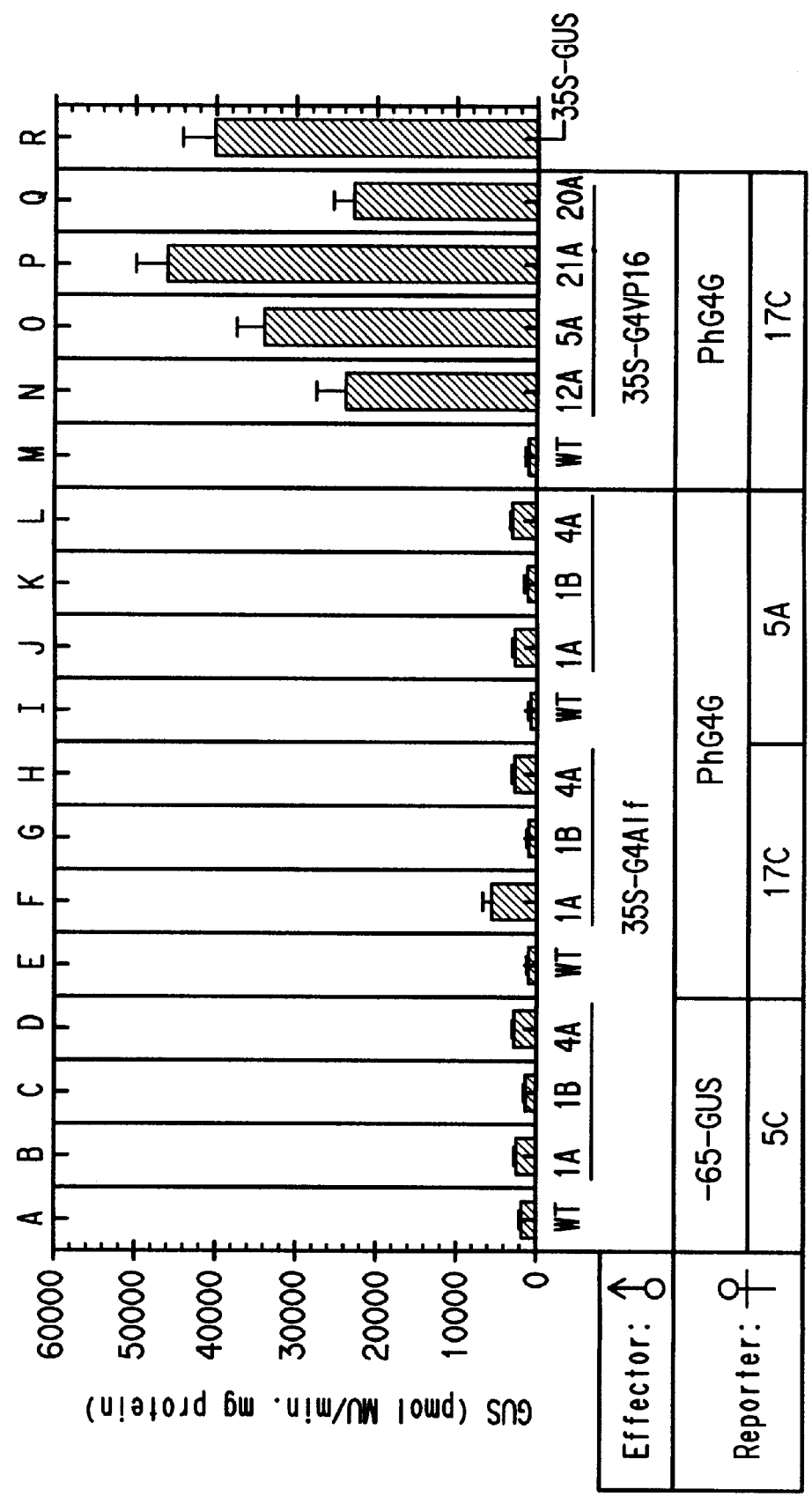

FIG. 21 presents the results of fluorometric assays demonstrating specific activation of the GUS reporter genes from −65-GUS and PhG4G by 35S-G4Alf or 35S-G4VP16 in transgenic tobacco seedlings. Genetic crosses were made between different reporter lines (−65-GUS 5C, PhG4G 17C, 5A) and different 35S-G4Alf lines (1A, 1B, 4A) or 35S-G4VP16 effector lines (12A, 5A, 21A, and 20A). One highly expressed transgenic line containing 35S-GUS was used as a control, giving a high level of constitutive gene expression.

SEQ ID NO: 1 is the consensus sequence for a Gal4 binding site.

SEQ ID NOS:2–6 are the sequences of the naturally occurring Gal4 binding sites as found in the promoters of genes for galactose catabolism in *Saccharomyces cerevisiae*.

SEQ ID NO:7 is the core sequence of the RY-G-box-RY element used in Example 3.

SEQ ID NO:8 is the sequence of the CACA box found in the glycinin 2 promoter.

SEQ ID NO:9 is the sequence of the legumin box element.

SEQ ID NOS: 10–12 are sequences of known variations of the RY box in the promoters of different legumin and glycinin genes.

SEQ ID NO:13 is the core sequence of the Gy2 element used in Example 4.

SEQ ID NOS:14–16 are DNA segments known to confer responsiveness to ABA and VP1.

SEQ ID NO:17 is core sequence of the Em regulatory element used in Example 5.

SEQ ID NO:18 is the core sequence of the C1 regulatory element used in Example 6.

SEQ ID NO:19 is the G-box regulatory element used in Example 7.

SEQ ID NOS:20 and 21 are the critical components of the CHS Unit I regulatory element used in Example 8.

SEQ ID NO:22 is the CHS Unit I used in Example 7.

SEQ ID NOS:23 and 24 are the oligonucleotides used to form the Gal4 binding site cassette described in Example 1.

SEQ ID NOS:25 and 26 are the oligonucleotides used to form the seed-specific RY-G-box-RY regulatory element cassette described in Example 3.

SEQ ID NOS:27 and 28 are the oligonucleotides used to form the glycinin 2 regulatory element cassette described in Example 4.

SEQ ID NOS:29 and 30 are the oligonucleotides used to form the Em regulatory element cassette described in Example 5.

SEQ ID NOS:31 and 32 are the oligonucleotides used to form the C1 regulatory element cassette described in Example 6.

SEQ ID NOS:33 and 34 are the oligonucleotides used to form the constitutive G-box regulatory element cassette described in Example 7.

SEQ ID NOS:35 and 36 are the oligonucleotides used to form the CHS Unit I regulatory element cassette described in Example 8.

BIOLOGICAL DEPOSIT

The following plasmid has been deposited under the terms of the Budapest Treaty with the American Type Culture Collection (ATCC), 12301 Parklawn Drive, Rockville, Md. 20852, and bears the following accession number:

| Plasmid | Accession Number | Date of Deposit |
|---------|------------------|-----------------|
| pZBL1   | ATCC 209128      | June 24, 1997   |

DETAILED DESCRIPTION OF THE INVENTION

The term "essentially similar" refers to nucleic acid fragments wherein changes in one or more nucleotide bases do not substantially effect the function of the nucleic acid fragment in binding of the DNA binding domain. "Essentially similar" also refers to a modification in one or more nucleotide bases that results in substitution of one or more amino acids, but does not affect the functional properties of the protein encoded by the DNA sequence. Thus "essentially similar" amino acid sequences are those that specify proteins having equivalent function. It is therefore understood that the invention encompasses more than the specific exemplary sequences.

The term "gene" refers to a nucleic acid fragment that expresses a specific protein or finctional RNA, including regulatory sequences preceding (5' non-coding sequences) and following (3' non-coding sequences) the coding sequence. "Chimeric gene" refers to any gene that comprises regulatory and coding sequences that are not found together in nature, or sequences encoding parts of proteins not naturally adjoined, or parts of promoters that are not naturally adjoined. Accordingly, a chimeric gene may comprise regulatory sequences and coding sequences that are derived from different sources, or regulatory sequences and coding sequences derived from the same source, but arranged in a manner different that that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. "Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include promoters, translation leader sequences, introns, and polyadenylation signal sequences.

"Promoter" refers to a DNA sequence involved in controlling the expression of a coding sequence or functional RNA. In general, a coding sequence is located 3' to a promoter sequence. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, Biochemistry of Plants 15:1–82, 1989. It is further recognized that since in most cases the exact boundaries of regulatory sequences have not been completely defined, DNA fragments of different lengths may have identical promoter activity.

"Regulatory element" refers to a DNA sequence that plays a role in determining promoter activity, i.e., a regulatory element can play a role in determining the activity of a regulatory sequence. Regulatory elements may affect the level, tissue/cell type specificity and/or developmental timing of expression. A "regulatory element" may be a part of a promoter, or it may be located upstream of a minimal promoter. DNA sequences considered to be regulatory elements include sequences that have been shown to be target sites for binding of transcription factors, as well as sequences whose properties have not yet been defined but are known to have a function because their deletion from a promoter affects the expression. "Constitutive" regulatory elements are those that direct expression in most tissues of the plant, throughout most of the plant developmental cycle. "Seed-specific" regulatory elements are those that direct expression in seed tissue during seed development. There are different types of seed-specific regulatory elements that may direct expression in different types of seed tissues or at different stages of seed development.

The "translation leader sequence" refers to a DNA sequence located between the promoter sequence of a gene and the coding sequence. The translation leader sequence is present in the fully processed MRNA upstream of the translation start sequence. The translation leader sequence may affect processing of the primary transcript to mRNA, mRNA stability or translation efficiency. (Turner, R. and Foster, G. D. (1995) Molecular Biotechnology 3:225).

The "3' non-coding sequences" refer to DNA sequences located downstream of a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671–680, 1989.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

A "finctional RNA" refers to an antisense RNA, ribozyme, or other RNA that is not translated.

The term "expression", as used herein, refers to the transcription of sense (mRNA) or antisense RNA. Expression also refers to translation of mRNA into a polypeptide.

As used herein "Gal4 binding site" means the nucleotide sequence shown in SEQ ID NO: 1, or any essentially similar sequences to which the Gal4 DNA binding domain can bind. In other words, the terms "Gal4 binding site" and "Gal4 binding sequence" are used interchangeably herein.

CGGAGGACAGTCCTCCG (SEQ ID NO:1)

The Gal4 binding sequence is the consensus sequence of the four Gal4 sites found in the Upstream Activation Sequence (UAS$_G$) controlling expression of the yeast GAL1 and GAL10 genes and the one Gal4 site found in the GAL7 promoter (Giniger et al., (1985) Cell 40:767–774). The original Gal4 site sequences are presented in SEQ ID NOS:2–6.

| CGGATTAGAAGCCGCCG | (SEQ ID NO:2) |
| CGGGTGACAGCCCTCCG | (SEQ ID NO:3) |
| AGGAAGACTCTCCTCCG | (SEQ ID NO:4) |
| CGCGCCGCACTGCTCCG | (SEQ ID NO:5) |
| CGGACAACTGTTGACCG | (SEQ ID NO:6) |

These different sequences demonstrate some of the variation that can be made in the Gal4 binding site while maintaining the ability of Gal4 to bind, and would be considered essentially similar sequences.

As used herein "Gal4 binding site promoter" refers to a promoter that is operably linked to at least one Gal4 site. Thus "Gal4 binding site promoter" may include combinations such as, but not limited to, at least one Gal4 binding sequence and a minimal promoter, at least one Gal4 binding sequence and additional regulatory elements with a minimal promoter, a promoter with at least one Gal4 binding sequence added, or a promoter with at least one Gal4 binding sequence and additional regulatory elements added.

As used herein, "activation domain" refers to a protein domain that has a stimulatory effect on transcription. Natural activation domains are portions of transcription factors that can be fused to DNA binding domains and shown to have transcription stimulatory effects. Natural activation domains can be altered, wherein amino acids are substituted or deleted, without altering the transcription stimulatory effects (Cress and Triezenberg, 1991, Science 251:87–90; Drysdale et al., 1995, Molecular and Cellular Biology 15:1220–1233).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein et al. (1987) Nature (London) 327:70–73; U.S. Pat. No. 4,945,050).

This invention provides for the first time a Gal4 chimeric transcription factor/target promoter system which functions in stably transformed plants. Specifically, the present invention concerns a method of regulating gene expression in a stably transformed transgenic plant cell which comprises combining into the genome of the plant cell:

a) a first chimeric gene comprising in the 5' to 3' direction:
  (1) a promoter operably linked to at least one Gal4 binding sequence;
  (2) a coding sequence or a complement thereof operably linked to the promoter; and
  (3) a polyadenylation signal sequence operably linked to the coding sequence or a complement thereof;
  provided that when the promoter is a minimal promoter then the Gal4 binding sequence is located upstream of the minimal promoter; and b) a second chimeric gene comprising in the 5' to 3' direction:
  (1) a promoter;
  (2) a DNA sequence encoding a DNA binding domain of a Gal4 transcriptional activator;
  (3) a DNA sequence encoding a transcriptional activation domain operably linked to the DNA sequence of (2); and
  (4) a polyadenylation signal sequence operably linked to the DNA sequence of (3);

wherein the expression of the second chimeric gene regulates expression of the first chimeric gene.

In another aspect, the first gene further can comprise at least one regulatory element.

The Gal4 binding site promoter in the first chimeric gene will be activated in the presence of the chimeric transcription factor produced by the second chimeric gene. It is well known in the art that the presence of multiple copies of a DNA binding site in a promoter can increase the effectiveness of the promoter (Carey et al., 1990 Nature 345: 361). Thus, the Gal4 binding site promoter in the first chimeric gene comprises at least one Gal4 binding site having the sequence set forth in SEQ ID NO: 1, or a sequence that is essentially similar. The second chimeric gene which encodes the chimeric transcription factor comprises the sequence encoding the DNA binding domain of Gal4, which includes at least the amino terminal 147 amino acids of the Gal4 protein, or an essentially similar sequence. The activation domain can be any sequence of amino acids that is capable of stimulating transcription. The activation domain is generally derived from a transcription factor or coactivator and is that portion of the protein that interacts with other proteins involved in transcription, thereby stimulating the transcription process. Thus, any activation domain which is capable of stimulating transcription can be used to practice the invention. The preferred activation domain should be an acidic transcriptional activation domain. Such activation domains can include, but are not limited to, those from the herpes simplex virus VP16 protein (Triezenberg et al., 1988 Genes Dev. 2: 718) and from the Phaseolus vulgaris PvAlf protein (Bobb et al., 1995 The Plant Journal 8: 101). Any plant cells, that can currently be transformed or will be transformable in the future, for example dicot or monocot cells, can be used to practice the present invention. Examples of dicot cells include, but are not limited to, cells from soybean, tomato, potato, tobacco, oilseed rape, sunflower, cotton, alfalfa, pea, sugarbeet, chick pea, lentil, lupin, french bean, lima bean. Examples of monocot cells include, but are not limited to, cells from maize, wheat, rye, barley, rice, sorghum.

A first chimeric gene comprising a Gal4 binding site promoter and a second chimeric gene encoding a chimeric Gal4 DNA binding domain/activation domain transcription factor can be introduced into the genome of plant cells using techniques well known to those skilled in the art. These methods include, but are not limited to, (1) direct DNA uptake, such as particle bombardment or electroporation (Klein et al. (1987) Nature (London) 327:70–73; U.S. Pat. No. 4,945,050), and (2) Agrobacterium-mediated transformation (De Blaere et al. (1987) Meth. Enzymol. 143:277).

The first chimeric gene comprising a Gal4 binding site promoter operably linked to a gene of interest and the second chimeric gene comprising a Gal4 DNA binding domain/ activation domain transcription factor are two separate components used to practice the invention. Each of these chimeric genes can be separately transformed into the genome of a plant species such that transformants harboring one component are distinct from transformants harboring the second component. The two components can then be combined into the genome of one plant by genetic crossing of the two transformants harboring the two separate components. Thus, the first and second chimeric genes can be combined into the genome of the plant cell by (a) transforming a plant cell with the first construct, (b) transforming a second plant cell with the second construct, (c) growing fertile mature plants from the transformed plant cells in (a) and (b) and (d) genetically crossing the transformed plants to produce progeny whose genome contains the first and second constructs.

Alternatively, the two components may be introduced together into the same genome by transformation of both components at the same time in the same cell. Still another means is for one component alone to be transformed into the genome, followed by a second transformation with the second component of the cells already harboring the first component.

Accordingly, in another aspect, this invention concerns plants transformed using the method of the invention and seeds obtained from such plants.

For the purpose of regulating transcription of a transgene containing the Gal4 binding site promoter, this promoter is operably linked to an untranslated leader, a coding region, a 3' untranslated sequence, and a polyadenylation signal sequence. Alternatively, the coding region may be replaced by a sequence that produces a finctional RNA that may, in turn, mediate control of gene expression by antisense, co-suppression or other gene expression technology.

The chimeric Gal4 DNA binding domain/activation domain transcription factor may be regulated by any constitutive, tissue-specific, or developmentally regulated promoter. This transcription factor in turn regulates expression of a transgene containing the Gal4 binding site promoter, i.e., a promoter operably linked to at least one Gal4 binding sequence. The Gal4 binding site promoter minimally contains at least one Gal4 binding site and a TATA box. Additional elements may be present in the Gal4 binding site promoter, such as a CAAT box, or binding sites for one or more transcription factors other than the chimeric Gal4 DNA binding domain/activation domain transcription factor. It is known in animal systems that targeting of some combinations of transcription factors to the same promoter may produce synergistic effects on the expression level (Lin et al., 1990 Nature 345: 359).

Further enhancement of gene activation by the instant two component system can be obtained by the addition of other regulatory elements in the Gal4 binding site promoter or upstream of a minimal promoter. Such additional regulatory elements can be, but are not limited to, seed-specific elements, constitutive elements, and enhancers. A variety of elements that are involved in regulating expression of genes during seed development have been identified. For example, the RY-G-box-RY regulatory element is commonly found in seed storage protein and lectin gene promoters and is necessary for positive regulation of seed-specific gene expression in the soybean glycinin and β-conglycinin seed storage protein promoters, and the French bean β-phaseolin seed storage protein promoter (Leliever et al., 1992, Plant Physiol. 98: 387–391; Bustos et al., 1991 EMBO J. 10: 1469–1479; Kawagoe et al., 1994 Plant J. 5: 885–890; Bobb et al., 1997 Nucleic Acids Research 25: 641–647; Dickinson et al., 1988, Nucleic Acids Research 16: 371; Fujiwara and Beachy 1994, Plant Molecular Biology 24: 261–272; Chamberland et al., 1992, Plant Molecular Biology 19: 937–949). The sequences of the RY-G-box-RY elements that are found in different natural promoters have variations, but can be recognized by the presence of particular nucleotide sequences: CATGCAW (the "RY" feature) and CACGTG (the "G-box"). One or more copies of the RY-G-box-RY element, shown in SEQ ID NO:7, or of sequence that is essentially similar, can be introduced in the Gal4 binding site promoter or upstream of a minimal promoter to increase the level of seed-specific gene expression in plants.

CATGCATGTCTACACGTGATCGCCATGCAA (SEQ ID NO:7)

The glycinin 2 (Gy2) regulatory element from the soybean glycinin 2 gene promoter contains both a CACA element and a legumin box, and is required for the high level seed-specific gene expression of this promoter (Leliever et al., 1992, Plant Physiol. 98: 387–391). The nucleotides that are recognized as the CACA and legumin box elements are presented in SEQ ID NOS:8 and 9, respectively.

```
TAACACA                   (SEQ ID NO:8)

TTCCATAGCCATGCATACTGAATGTCT  (SEQ ID NO:9)
```

In promoters of different legumin and glycinin genes there are variations in the RY box of the legumin box. Examples are shown is SEQ ID NOS:10–12 (Dickinson et al., 1988, Nucleic Acids Res. 16:371)

```
CATGCATG        (SEQ ID NO:10)

CATGCAAG        (SEQ ID NO:11)

CATGCATA        (SEQ ID NO:12)
```

One or more copies of the Gy2 element, as shown is SEQ ID NO:13, or of sequence that is essentially similar, can also be used in combination with the Gal4 binding sites to increase the level of seed-specific gene expression in plants.

TAACACACAAGGCTTCCATAGCCATG-
CATACTGAAGAATGTCT (SEQ ID NO:13)

The Em regulatory element, including Em1 a, Em2 and Em1b elements from the wheat Em gene promoter, is strongly linked to regulation by abscissic acid (ABA) and to the maize transcription factor VP1 in transient assays with maize protoplasts (Marcotte et al., 1989, Plant Cell 1: 969–976; Vasil et al., 1995, Plant Cell 7: 1511–1518). Both ABA and VP1 are involved in regulating expression of genes during seed development. The nucleic acid segments that are recognized as the ABA and VP1 responsive elements are shown in SEQ ID NOS:14–16.

```
GGACACGTGGC          (SEQ ID NO:14)
CGAGCAGGC            (SEQ ID NO:15)
GCACACGTGCC          (SEQ ID NO:16)
```

One or more copies of the Em element as shown in SEQ ID NO: 17, or of sequence that is essentially similar, can also be used in combination with the Gal4 binding sites to increase the level of seed-specific gene expression in plants.

```
GGACACGTGGCGCGACAGCAGGGACAAC-
GAGCAGGCCGACGCACGTCCGCGTC GCT
GCACACGTGCC          (SEQ ID NO:17)
```

The C1 regulatory element, including the GT element and the SphI element from the maize C1 gene promoter, is essential for ABA regulation and VP1 trans-activation (Hattori et al., 1992, Gene & Development 6: 609–618; Kao et al., 1996, Plant Cell 8: 1171–1179). One or more copies of the C1 element, as shown in SEQ ID NO: 18, or of sequence that is essentially similar, can also be used in combination with the Gal4 binding sites to increase the level of seed-specific gene expression in plants.

```
GTGTCGTGTCGTCCATGCATGCAC    (SEQ ID NO: 18)
```

The G-box (CACGTG) is a hexameric element found in many diverse plant gene promoters. There are many different kinds of G-box binding factors with different binding specificites and affinities to their target sites. The sequences flanking the ACGT core affect the binding specificity of the G-box binding factors (Menkens et al., 1995, TIBS 20: 506–510; Katagiri and Chua, 1992, Trends in Genetics 8: 22–27; Foster and Chua, 1994, FASEB 8: 192–200). One or more copies of the DNA segment containing a G-box motif, as shown in SEQ ID NO:19, or a sequence that is essentially similar, can be used in combination with the Gal4 binding sites to increase the level of constitutive gene expression or tissue-specific gene expression in plants.

```
TCCACGTGGC           (SEQ ID NO:19)
```

Combinations between different G-box sequences and Gal4 binding sites can lead to diversity and specificity of plant gene expression in different tissues and organs. The CHS Unit I of the chalcone synthase gene promoter from parsley is a light-inducible element required for specific gene activation in light responsiveness (Weisshaar et al., 1991, EMBO J. 10: 1777–1786; Menkens et al., 1995, TIBS 20: 506–510). The nucleotides of this element that are recognized as being important for light responsiveness are shown in SEQ ID NOS:20 and 21.

```
CCACGTGGCC           (SEQ ID NO:20)
GTCCCTCCAACCTAACC    (SEQ ID NO:21).
```

One or more copies of the CHS Unit I, as shown in SEQ ID NO:22, or a sequence that is essentially similar, especially in combination with the Gal4 binding sites, can be used to increase the level of constitutive gene expression.

```
CCACGTGGCCATCCGGTGGCCGTCCCTCCA
ACCTAACC             (SEQ ID NO:22)
```

Another type of regulatory element that can improve gene activation by the instant two component system is an enhancer element. Any enhancer can be added to the Gal4 binding site promoter, optionally with the RY-G-box-RY element, Gy2 element, Em element, C1 element, G-box element, or CHS Uint I element. Examples of enhancers are the AT-rich enhancer from the phaseolin promoter (van der Geest et al., 1994 The Plant Journal 6 p 413–423; van der Geest et al., 1997, Plant Molecular Biology 33: 553–557), the OCS enhancer from the octopine synthase gene (Greve et al., 1983, J. of Molecular and Applied Genetics 1: 499–511), and the enhancer from the Cauliflower Mosaic Virus 35S promoter (Odell et al., 1988, Plant Molecular Biology 10:263–272).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Plasmid vectors comprising the instant chimeric genes are constructed using conventional techniques well known to those skilled in the art. The choice of plasmid vector is dependent upon the method that will be used to transform host plants and the desired selection markers. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411–2418,1985; De Almeida et al., MGG 218:78–86, 1989), and thus that multiple events must be screened in order to obtain lines displaying the desired expression level and pattern. Such screening may be accomplished using conventional techniques well known to those skilled in the art such as Southern analysis of DNA, Northern analysis of MRNA expression, Western analysis of protein expression, or phenotypic analysis.

The instant invention improves upon the available means of expressing transgenes by providing a method to regulate transgene expression in stably transformed plants. The method of the invention provides a means to achieve 1) a higher expression level than the level expressed from a commonly used, highly expressed seed storage protein gene promoter, 2) activation of expression in the grain following a cross, 3) coordinate regulation of multiple transgenes, and 4) amplification of the expression level while maintaining the expression pattern of a tissue-specific or developmentally regulated promoter.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Construction of Gal4 Binding Site Promoter-GUS Reporter Gene

A promoter consisting of four Gal4 binding sites and a phaseolin minimal promoter extending 5' to −65 was constructed 5' to a beta-glucuronidase (GUS) coding region and a phaseolin 3' polyadenylation signal sequence region. The four segments of this chimeric gene called G4G consist of the following: (1) Oligonucleotides containing four copies of the Gal4 DNA binding site consensus sequence as set forth is SEQ ID NO: 1 (Brasselman et al., 1993, PNAS 90: 1657) and terminal restriction sites. These oligonucleotides have the sequences shown in SEQ ID NOS:23 and24.

```
TCACCGGATCCTACGGAGGACAGTCCTCCGATTTACGGAGGACAGTCCTCCGAA (SEQ ID NO:23)

TATCGATAACGGAGGACAGTCCTCCGATTTACGGAGGACAGTCCTCCGAATTAT

CTGCAGAATAA

TTATTCTGCAGATAATTCGGAGGACTGTCCTCCGTAAATCGGAGGACTGTCCTCC(SEQ ID NO:24)

GTTATCGATATTCGGAGGACTGTCCTCCGTAAATCGGAGGACTGTCCTCCGTAG

GATCCGGTGA
```

Figure 1:
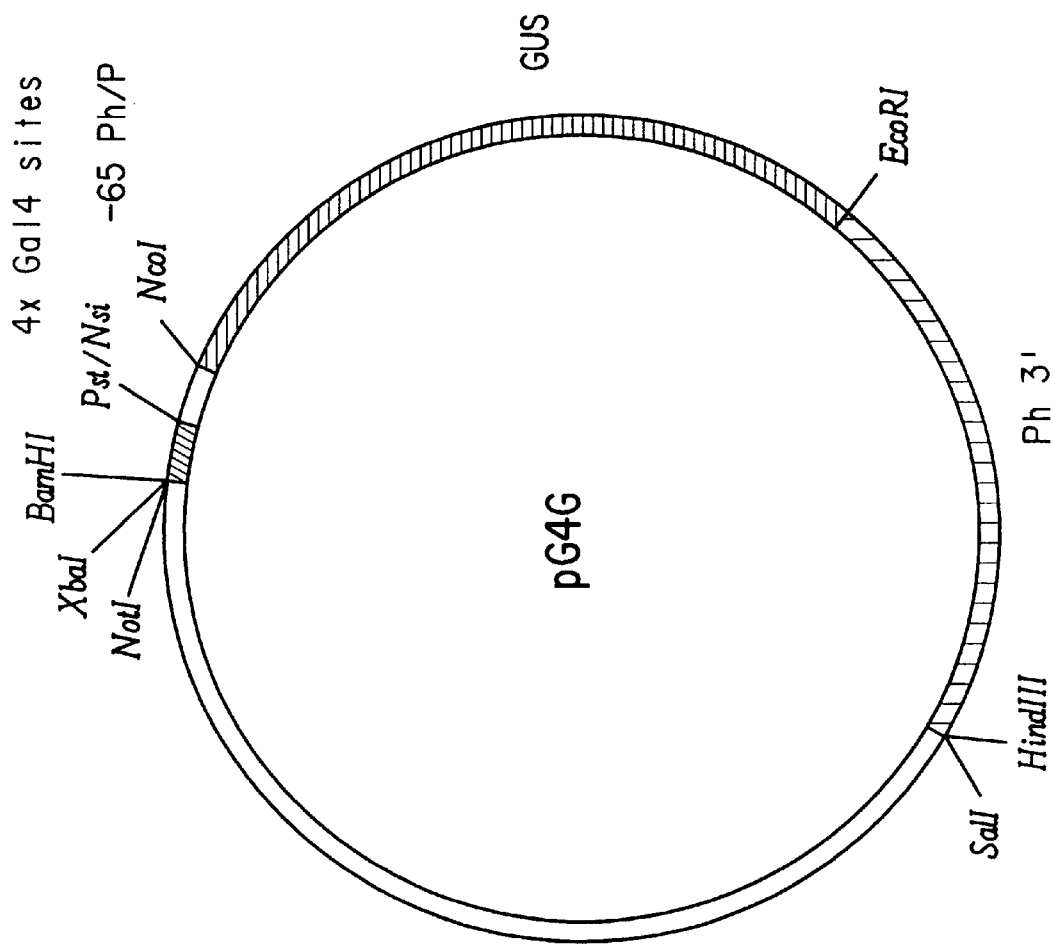
FIG. 1 is a map of plasmid pG4G which contains the chimeric G4G gene in pGEM9Zf. The G4G gene consists of 4 Gal4 binding sites, the −65 phaseolin promoter region and leader, the GUS coding region, and a phaseolin 3' polyadenylation signal sequence region.
Figure 2:
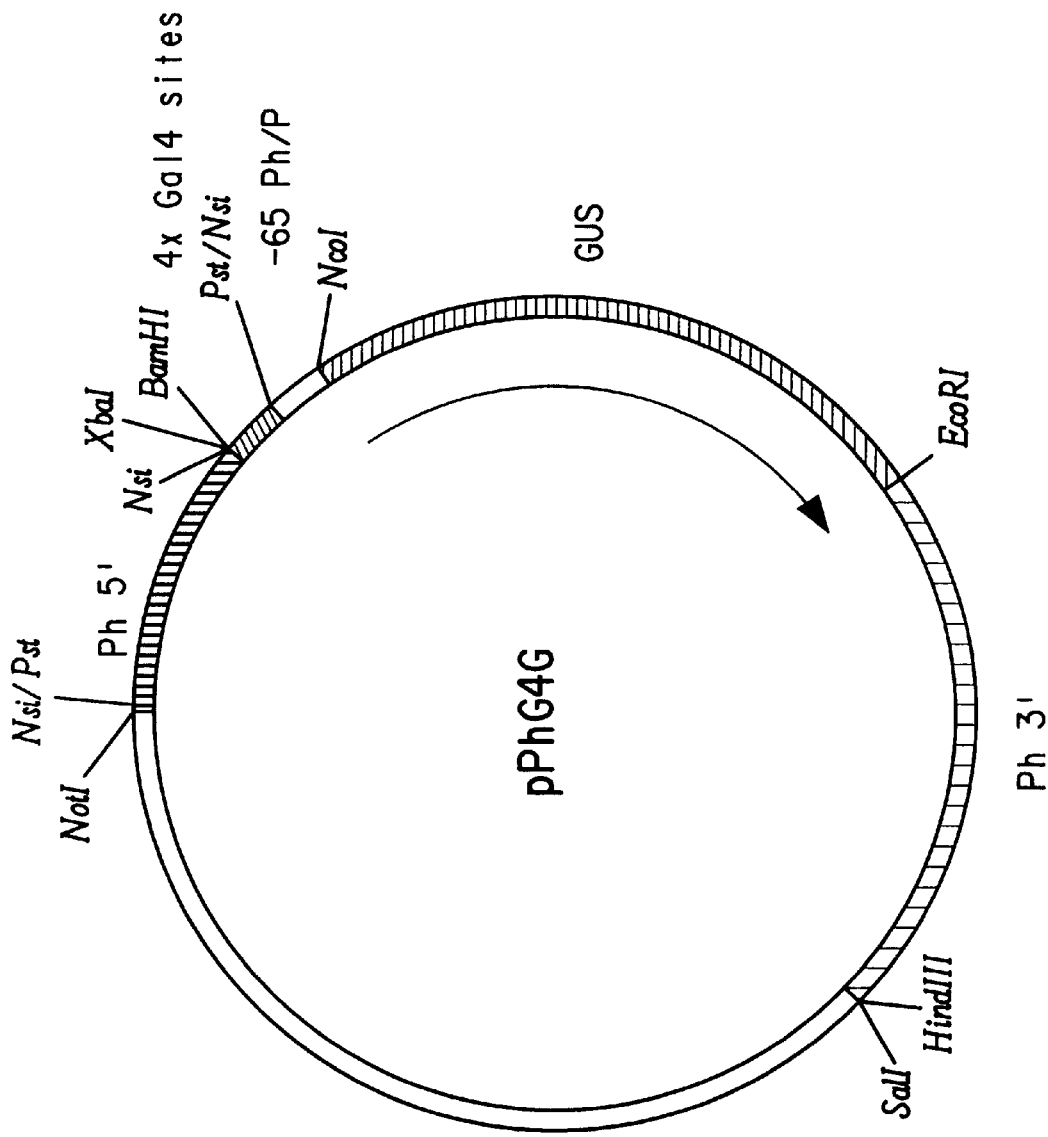
FIG. 2 is a map of plasmid pPhG4G. This is a modified form of pG4G; it has an additional sequence from the 5' upstream region of the phaseolin promoter that was added upstream of the G4G gene.

The double stranded DNA fragment resulting from annealing of these two oligonucleotides has a 5' BanHI site and a 3' PstI site. (2) An NsiI-NcoI fragment extending from −65 of the phaseolin promoter to +77 with respect to the transcription start site. The NcoI site had been added previously (Slightom et al., 1991 Plant Mol Biol Man B16: 1). PstI and NsiI ends anneal and ligate without regenerating a restriction site. (3) An NcoI-EcoRI fragment containing the uida coding region (GUS; Jefferson et a;., 1987 EMBO J 6: 3901). (4) A 1.2 kb EcoRI-HindIII fragment containing the phaseolin polyadenylation signal sequence region (Slightom et al., 1991 Plant Mol Biol Man B16: 1). The chimeric G4G gene with NotI and XbaI sites added to the 5' BamHI site in plasmid pGEM9Zf is called pG4G (FIG. 1). This chimeric gene was cloned as a BamHI-SalI fragment, after addition of the SalI site 3' to the HindIII site, into the Agrobacterium tumefaciens binary vector pZBL1 creating pZBL3. pZBL1 contains the origin of replication from pBR322, the bacterial nptI kanamycin resistance gene, the replication and stability regions of the pseudomonas aeruginosa plasmid pVS1 (Itoh et al., 1984), T-DNA borders described by van den Elzen et al., 1985 wherein the OCS enhancer (extending from −320 to −116 of the OCS promoter; Greve et al., 1983, Journal of Molecular and Applied Genetics 1: 499–511) that is a part of the right border fragment is removed, and a Nos/P-nptII-Ocs 3' gene to serve as a kanamycin resistant plant selection marker. Plasmid pZBL1 has been deposited with the ATCC and bears accession number 209128.

A second chimeric gene with Gal4 binding sites in the promoter was constructed identically to G4G with the addition of a DNA fragment located 5' to the four Gal4 binding sites. This additional DNA fragment is derived from the upstream portion of the phaseolin promoter and is the 1.08 kilobase DNA fragment bounded by the EcoRI site at −1471 and the NsiI site at −391, and containing a matrix attachment region and an AT-rich enhancer (obtained from Tim Hall, Texas A&M University; van der Geest et al., 1994 The Plant Journal 6 p 413–423, van der Geest and Hall, 1997, Plant Molecular Biology 33: 553–557). The partial sequence of this DNA fragment (−890 to −391) is available (GenBank Accession #J01263 M13758) from which a probe can be made to isolate the full EcoRi-NsiI fragment. A PstI (polylinker site) -NsiI fragment containing these sequences was subcloned into the NsiI site of pGEM9Zf vector so that it could be removed as a NotI-XbaI fragment and then added to the G4G gene to create PhG4G. To construct the PhG4G gene in a binary vector, first a BamHI site was added 5' to the PhG4G gene and then the BamHI-BamHI fragment containing the phaseolin promoter upstream sequence (Ph5') was cloned into the BamHI site upstream of the Gal4 sites in the binary pZBL3 vector to form pZBL7. The correct orientation of the Ph5' fragment was confirmed by restriction enzyme analysis.

A control construct, −65-GUS, consisting of a phaseolin −65 minimal promoter fused to the GUS coding region and the phaseolin 3' polyadenylation signal sequence region was made by fusing an Nsi-XbaI fragment containing the phaseolin −65 promoter and GUS coding region with an XbaI-HindIII fragment containing the phaseolin 3' region into the PstI and HindIII sites of the pSP72 vector. This chimeric gene, with no Gal4 sites, was cloned as a BamHI-XhoI fragment into the BamHI and SalI sites in the binary vector pZBL1 to form pZBL2.

Example 2

Construction of Chimeric Gal4 Transcription Activators

A chimeric Gal4 -PvAlf transcription activator was constructed under control of either a −410 phaseolin promoter (Ph/P-G4Alf) or a 35S promoter-Cab leader (35S-G4Alf). The Ph/P-G4Alf chimeric activator gene has four segments: (1) a 494 bp HindIII-NcoI fragment of the phaseolin promoter, extending to −410 and including leader sequences to +77 (Slightom et al., 1991 Plant Mol Biol Man B16: 1), (2) an NcoI-SmaI fragment encoding the N-terminal 147 amino acids of the Gal4 DNA binding domain (Ma et al., 1988 Nature 334: 631), (3) a SmaI-SalI fragment encoding the N terminal 243 amino acids of the PvAlf activation domain (Bobb et al., 1995 Plant J 8 p 101–113), (4) a 1.2 kb SalI-HindIII fragment containing the phaseolin 3' sequence. In the 35S-G4Alf chimeric activator gene, a 1.4 kb HindIII-NcoI fragment of the 35S promoter and Cab leader was used to replace the −410 phaseolin promoter and leader sequence in the Ph/P-G4Alf chimeric gene. The CaMV 35S promoter+chlorophyll a/b binding protein (cab) leader includes 35S promoter sequences extending to 8 bp beyond (3' to) the transcription start site operably linked to a 60 bp untranslated leader DNA fragment derived from the cab gene 22L (Harpster et al. 1988 Mol. Gen. Genet 212: 182).

Another chimeric Gal4 -VP 16 transcription activator was also made under control of either a −410 phaseolin promoter (Ph/P-G4VP 16) or a 35S promoter-Cab leader (35S-G4VP16). A 696 bp NcoI-BamHI (BamH I blunted) fragment encoding both the N-terminal 147 amino acids of the Gal4 DNA binding domain and the C-terminal 78 amino acids of the Herpes simples virus VP16 activation domain (Triezenberg et al., 1988 Genes and Dev. 2: 718) was cloned into the NcoI site and the SmaI site of the Ph/P-G4Alf or 35S-G4Alf to replace the G4Alf segments.

Each chimeric activator gene was first cloned as a HindIII fragment into the HindIII site pSK vector which had a second KpnI site added between the Bam HI and XbaI polylinker sites. The chimeric activator expression cassette was then cut out as a KpnI fragment and cloned into the KpnI site of the binary vector pZ5KAD creating pZ5KAD-Ph/P-G4Alf, pZ5KAD-35S-G4Alf, pZ5KAD-Ph/P-G4VP16, pZ5KAD-35S-G4VP16. The binary vector pZ5KAD contains the origin of replication from PBR322, the bacterial kanamycin nptI resistance gene, the replication and stability regions of the Pseudomonas plasmid pVS1 (Itoh et al., 1984), T-DNA borders (van den Elzen et al., 1985), and a 35S/$^R$-ALSP-ALS 3' gene to serve as a sulfonylurea resistant plant selection marker.

Each binary vector construction was transformed into *Agrobacterium tumefaciens* LBA4404, which was then used to inoculate tobacco leaf tissue. Transgenic tobacco plants were obtained essentially by the procedure of De Blaere et al., 1987 Meth. Enzymol. 143:277. Selection for transformed shoots was on either 20–50 ppb chlorsulfuron or 100 mg kanamycin/l . Shoots were rooted on either 20 mg chlorsulfuron/l or 100 mg kanamycin/l.

Example 3

Addition of Seed-Specific RY-G-Box-RY Regulatory Element to Gal4 Binding Site Promoter Oligonucleotides containing two copies of the RY-G-box-RY element consensus sequence (Conceicao and Krebbers, 1994 Plant J. 5: 493–505; Bustos et al., 1991 EMBO J. 10: 1469–1479; Kawagoe et al., 1994 Plant J. 5: 885–890; Bobb et al., 1997 Nucleic Acids Research 25: 641–647; Dickinson et al., 1988, Nucleic Acids Research 16: 371; Fujiwara and Beachy 1994, Plant Molecular Biology 24: 261–272; Chamberland et al., 1992, Plant Molecular Biology 19: 937–949) and terminal restriction BamH I sites were designed. These oligonucleotides have the sequences shown in SEQ ID NOS: 25 and 26.

The double stranded DNA fragment resulting from annealing of these two oligonucleotides has BamH I sites at both 5' and 3' ends. The 5' BamH I site was a perfect one which can be cut again by BamH I after cloning. The 3' BamH I site can only be used for ligation. The annealed DNA fragment was cloned directly into the BamH I site upstream of the four copies of the Gal4 binding site of G4G to form (RY-G-Box-RY)$_2$-G4G. The direct orientation of this RY-G-box-RY element upstream of the Gal4 sites was confirmed by BamH I digest. The chimeric (RY-G-box-RY)$_2$-G4G gene was cloned as a BamHI-SalI fragment into the binary vector pZBL1 creating pZBL4 as described in Example 1.

Example 4

Addition of Glycinin 2 Regulatory Element to Gal4 Binding Site Promoter

Oligonucleotides containing two copies of the Glycinin 2 (Gy2) element (CACA element plus legumin box) from the glycinin 2 gene of legumes (Lelievre et al., 1992, Plant Physiology 98: 387–391) and terminal restriction BamH I sites were designed. These oligonucleotides have the sequences shown in SEQ ID NOS: 27 and 28.

```
GATCCGTGTAACACACAAGGCTTCCATAGCCATGCATACTGAAGAATGTCTCAA      (SEQ ID NO:27)

TGGCTCACCCCTCGAGCTGCAGTAGCATGCTTCAGTCTGTGTGTAACACACAAG

GCTTCCATAGCCATGCATACTGAAGAATGTCTCAA

GATCTTGAGACATTCTTCAGTATGCATGGCTATGGAAGCCTTGTGTGTTACACAC    (SEQ ID NO:28)

AGACTGAAGCATGCTACTGCAGCTCGAGGGGTGAGCCATTGAGACATTCTTCAG

TATGCATGGCTATGGAAGCCTTGTGTGTTACACG
```

The double stranded DNA fragment resulting from annealing of these two oligonucleotides has BamH I sites at both 5' and 3' ends. The annealed DNA fragment was cloned directly into the BamH I site upstream of the four copies of the Gal4 binding site in G4G to form (Gy2)$_2$-G4G as described in Example 3.

Example 5

Addition of ABA-and VP1-Regulated Em Regulatory Element to Gal4 Binding Site Promoter Oligonucleotides containing two copies of the Em element consensus sequence (extending from −152 to −78 from the transcription start site of the wheat Em promoter; Marcotte et al., 1989, Plant Cell 1: 969–976; Vasil et al., 1995, Plant Cell 7: 1511–1518) and terminal restriction BamH I sites were designed. These oligonucleotides have the sequences shown in SEQ ID NOS: 29 and 30.

```
GATCCTGCATGCATGTCTACACGTGATCGCCATGCAATTTGGCTCACCCCTCGAG    (SEQ ID NO:25)

CTGCAGTAGCATGCTTCAGTCTGTTGCATGCATGTCTACACGTGATCGCCATGCA

ATT

GATCAATTGCATGGCGATCACGTGTAGACATGCATGCAACAGACTGAAGCATGC    (SEQ ID NO:26)

TACTGCAGCTCGAGGGGTAGGCCAAATTGCATGGCGATCACGTGTAGACATGCA

TGCAG
```

```
GATCCTGCCGGACACGTGGCGCGACAGCAGGGACAACGAGCAGGCCGACGCAC    (SEQ ID NO:29)

GTCCGCGTCGCTGCACACGTGCCGCCTTGGCTCACCCCTCGAGCTGCAGTAGCA

TGCTTCAGTCTGTTGCCGGACACGTGGCGCGACAGCAGGGACAACGAGCAGGC

CGACGCACGTCCGCGTCGCTGCACACGTGCCGCCT

GATCAGGCGGCACGTGTGCAGCGACGCGGACGTGCGTCGGCCTGCTCGTTGTCC    (SEQ ID NO:30)

CTGCTGTCGCGCCACGTGTCCGGCAACAGACTGAAGCATGCTACTGCAGCTCGA

GGGGTGAGCCAAGGCGGCACGTGTGCAGCGACGCGGACGTGCGTCGGCCTGCT

CGTTGTCCCTGCTGTCGCGCCACGTGTCCGGCAG
```

The double stranded DNA fragment resulting from annealing of these two oligonucleotides has BamH I sites at both 5' and 3' ends. The annealed DNA fragment was cloned directly into the BamH I site upstream of the four copies of the Gal4 binding site in G4G to form (Em)$_2$-G4G as described in Example 3. The chimeric (Em)$_2$-G4G gene was cloned as a BamHI-SalI fragment into the binary vector pZBL1 creating pZBL5 as described in Example 1.

506–510; Katagiri and Chua, 1992, Trends in Genetics 8: 22–27; Foster and Chua, 1994, FASEB 8: 192–200) and terminal restriction BamH I sites were designed. These oligonucleotides have the sequences shown in SEQ ID NOS: 33 and 34.

```
GATCCTCCACGTGGCTATTCAATACTCCACGTGGCTGGCTCACCCCTCGAGCTGC    (SEQ ID NO:33)

AGTAGCATGCTTCAGTCTGTTCCACGTGGCTTCAAGATTTTCCACGTGGC

GATCGCCACGTGGAAAATCTTGAAGCCACGTGGAACAGACTGAAGCATGCTACT    (SEQ ID NO:34)

GCAGCTCGAGGGGTGAGCCAGCCACGTGGAGTATTGAATAGCCACGTGGAG
```

Example 6

Addition of ABA- and VP1-Regulated C1 Regulatory Element to Gal4 Binding Site Promoter Oligonucleotides containing two copies of the C1 element (including the GT-element and the SphI element) (Hattori et al., 1992, Gene & Development 6: 609–618; Kao et al., 1996, Plant Cell 8: 1171–1179) and terminal restriction BamH I sites were designed. These oligonucleotides have the sequences shown in SEQ ID NOS: 31 and 32.

```
GATCCGCAGTGTCGTGTCGTCCATGCATGCACTTTTGGCTCACCCCTCGAGCTGC    (SEQ ID NO:31)

AGTAGCATGCTTCAGTCTGTGCAGTGTCGTGTCGTCCATGCATGCACTTT

CATGCTACTGCAGCTCGAGGGGTGAGCCAAAAGTGCATGCATGGACGACACGA    (SEQ ID NO:32)

CACGATCAAAGTGCATGCATGGACGACACGACACTGCACAGACTGAAGTGCG
```

The double stranded DNA fragment resulting from annealing of these two oligonucleotides has BamH I sites at both 5' and 3' ends. The annealed DNA fragment was cloned directly into the BamH I site upstream of the four copies of the Gal4 binding site in G4G to form (C1)$_2$-G4G as described in Example 3.

Example 7

Addition of Constitutive G-box Regulatory Element to Gal4 Binding Site Promoter Oligonucleotides containing four copies of the G-box element, TCCACGTGGC (Menkens et al., 1995, TIBS 20:

The double stranded DNA fragment resulting from annealing of these two oligonucleotides has BamH I sites at both 5' and 3' ends. The annealed DNA fragment was cloned directly into the BamH I site upstream of the four copies of the Gal4 binding site in G4G to form (G-box)$_4$-G4G as described in Example 3. The chimeric (G-box)$_4$-G4G gene was cloned as a BamHI-SalI fragment into the binary vector pZBL1 creating pZBL6 as described in Example 1.

Example 8

Addition of Light-Inducible CHS Unit I Regulatory Element to Gal4 Binding Site Promoter Oligonucleotides containing two copies of the CHS Unit I element of the chalcone synthase gene from parsley (including box I and box II; Weisshaar et al., 1991, EMBO J. 10: 1777–1786; Menkens et al., 1995, TIBS 20: 506–510) and terminal restriction BamH I sites were designed. These oligonucleotides have the sequences shown in SEQ ID NOS: 35 and 36.

```
GATCCCCTTATTCCACGTGGCCATCCGGTGGCCGTCCCTCCAACCTAACCTCCCT    (SEQ ID NO:35)

TGTGGCTCACCCCTCGAGCTGCAGTAGCATGCTTCAGTCTGTCCTTATTCCACGT

GGCCATCCGGTGGCCGTCCCTCCAACCTAACCTCCCTTG

GATCCAAGGGAGGTTAGGTTGGAGGGACGGCCACCGGATGGCCACGTGGAATA     (SEQ ID NO:36)

AGGACAGACTGAAGCATGCATCTGCAGCTCGAGGGGTGAGCCACAAGGGAGGT

TAGGTTGGAGGGACGGCCACCGGATGGCCACGTGGAATAAGGG
```

Each copy of the CHS Unit I element is underlined and conserved nucleotides are in bold type. The double stranded DNA fragment resulting from annealing of these two oligonucleotides has BamH I sites at both 5' and 3' ends. The annealed DNA fragment was cloned directly into the BamH I site upstream of the four copies of the Gal4 binding site in G4G to form (CHS-Unit I)$_2$-G4G as described in Example 3.

Example 9

Addition of Phaseolin AT-Rich Enhancer to (RY-G-Box-RY)$_2$-Gal4 Binding Site Promoter An additional enhancer DNA fragment was introduced upstream of the (RY-G-box-RY)$_2$-Gal4 binding sites. As described in Example 1, this AT-rich enhancer was derived from the upstream portion of the phaseolin promoter (Ph5') extending from an EcoRI site at -1471 to an NsiI site at -391, and containing a matrix attachment region and an AT-rich enhancer (obtained from Tim Hall, Texas A&M University; van der Geest et al., 1994, The Plant Journal 6 p 413–423; van der Geest and Hall, 1997, Plant Molecular Biology 33: 553–557). To construct the Ph5'-(RY-G-Box-RY)$_2$-G4G gene in a binary vector, the BamHI-BamHI fragment containing Ph5' as described in Example 1 was cloned into the BamHI site upstream of the (RY-G-box-RY)$_2$-Gal4 sites in the binary pZBL4 vector to form pZBL8. The correct orientation of the Ph5' fragment was confirmed by restriction enzyme analysis.

Example 10

Addition of Phaseolin AT-Rich Enhancer to (Em)$_2$-Gal4 Binding Site Promoter As in Example 9, the phaseolin AT-rich enhancer was also introduced into the (Em)$_2$-Gal4 binding site promoter-GUS reporter gene. To construct the Ph5'-(Em)$_2$-G4G gene in a binary vector, the BamHI-BamHI fragment containing Ph5' as described in Example 1 was cloned into the BamHI site upstream of the (Em)$_2$-Gal4 sites in the binary pZBL5 vector to form pZBL9. The correct orientation of the Ph5' fragment was confirmed by restriction enzyme analysis.

Example 11

Addition of Phaseolin AT-rich Enhancer to (G-Box)$_4$-Gal4 Binding Site Promoter As in Example 9, the phaseolin AT-rich enhancer was also introduced into the (G-box)$_4$-Gal4 binding site promoter-GUS reporter gene. To construct the Ph5'-(G-box)$_4$-G4G gene in a binary vector, the BamHI-BamHI fragment containing Ph5' as described in Example 1 was cloned into the BamHI site upstream of the (G-box)$_4$-Gal4 sites in the binary pZBL6 vector to form pZBL10. The correct orientation of the Ph5' fragment was confirmed by restriction enzyme analysis.

Example 12

Genetic Crossing of Transgenic Tobacco Plants

Primary transformants were transferred to soil and grown in a growth chamber maintained for a 14 hr, 21° C. day, 10 hr, 18° C. night cycle, with approximately 80% relative humidity, under mixed cool white fluorescent and incandescent lights. Plants were grown to maturity and hand pollinations were performed using a slight modification of the procedure by Wernsman, E. A. and D. F. Matzinger in *Hybridization of Crop Plants* W. R. Fehr and H. H. Hadley, eds, pp 657–668 (1980). Briefly, flowers from plants to be used as the female parents were selected on the day before anthesis; the corolla was split longitudinally, the anthers were removed, and the stigma was pollinated with pollen from flowers from male parent plants that were allowed to anthese on the plant. To prevent contaminating pollen from reaching the stigma, a 4 cm length of a cocktail stirrer, one end plugged with modeling clay, was slipped over the stigma and style and held in place by the corolla. Each flower was tagged. Capsules were allowed to grow to maturity and then harvested.

Genetic crossing was conducted at the R$_0$ generation (primary transformants) between the effector plants carrying a chimeric transcription factor and reporter plants carrying a Gal4 binding site promoter-GUS gene. Three independent transgenic tobacco plants containing a reporter gene were individually crossed to three independent transgenic lines containing an effector gene. The reporter plants were also crossed to the wild type tobacco plants serving as a control for the gene expression level in the absence of effectors.

Example 13

Assay of Transgene Expression in Seed

F$_1$ seeds from genetic crosses were analyzed for GUS activities. For each sample about 100 seeds (30 mg) were quickly frozen in liquid N$_2$ and ground in 0.5 ml GUS lysis buffer (50 mM NaH$_2$PO$_4$/Na$_2$HPO$_4$, pH 7, 10 mM EDTA, 0.1% Triton X-100, 0.1% Sarkosyl, 10 mM b-Mercaptoethanol). Following a 15 min high speed centrifugation at 4° C., the supernatant was collected and stored at -70° C. until assayed. For the GUS assay, 25 μl of GUS lysis buffer was first added into each individual well of a 96-well fluorometric microtitre plate (Titretek Fluoroplate; ICN Biomedicals). One microliter of each sample extract was added into the 25 μl of GUS lysis buffer in each well. One hundred and fifty microliters of freshly prepared MUG substrate (1.7 mM 4-methylumbelliferyl-b-D glucuronide (Sigma) in GUS lysis buffer) was added to each well. The reaction was stopped by adding 75 μl of 0.6 M $Na_2CO_3$ at 0, 30, 60, and 120 minutes after addition of MUG substrate. Fluorescence was detected and quantified using a Perkin-Elmer LS-3B spectrometer. Sample activities were determined from a standard curve constructed by plotting the amount of MU standards (pmol) versus their measured fluorescence intensities. Protein assays were performed on the same sample extracts using the Bio-rad Protein Assay System (Hercules, Calif.) following the manufacturer's instructions for the microtitre plate protocol. GUS activities were then calculated as pmol/min/mg protein.

As shown in FIGS. 9–12, the chimeric G4VP 16 and G4Alf transcription factors, under control of either the phaseolin promoter or 35S promoter, specifically activated the Gal4 binding site promoter. This gene activation required specific Gal4 binding sites in the responsive promoters, since gene activation was not detected in the pZBL2 reporter lines, which are the control with no Gal4 sites in the promoter.

For example, in FIG. 9 lanes I-L show GUS activities in $F_1$ seed resulting from crossing pZBL3 line 2A (which carries the reporter gene, i.e., the GUS gene driven by the Gal4 binding site promoter) with plants of either wild type (WT) or Ph/P-G4VP16 lines 14A, 15A, or 13B (which, with the exception of the wild type negative control, carry the chimeric transcription factor under the control of the seed specific phaseolin promoter). Lane I thus shows the background level of expression when no chimeric transcription factor is provided; J-L show the range of expression levels which were obtained with both components of the system present. All are clearly higher than the control, indicating that the chimeric transcription factor is activating transcription above the background level. More crosses were done using three additional pZBL3 transgenic lines. Lanes M-R show the results of crossing reporter lines pZBL3 6A, 4B, and 3D with a single Ph/P-G4VP16 line 14A (lanes N, P, R) and the WT control (lanes M, O, Q). Again the chimeric transcription factor activates GUS expression well above background levels in all crosses.

The specificity of this gene activation system was also demonstrated. Lanes A and B show GUS activities in $F_1$ seed resulting from crossing a control plant pZBL2 2C (a minimal promoter lacking Gal4 binding sites) with WT or Ph/P-G4VP 16 line 14A. Lanes C-F show GUS activities in $F_1$ seed resulting from crossing a control plant pZBL2 11A with WT or Ph/P-G4VP16 lines 14A, 15A or 13B. Lanes G-H show GUS activities in $F_1$ seed resulting from crossing a control plant pZBL2 4B with WT or Ph/P-G4VP16 line 14A. With no Gal4 binding sites present no activation is observed.

FIGS. 10–21 are read in a similar manner as described for FIG. 9.

As shown in FIGS. 13–16, the ABA-and VP1-regulated Em element or constitutively regulated G-box element were also used in combination with the Gal4 binding sites. The chimeric G4VP 16 and G4Alf transcription factors, under control of either the phaseolin promoter or 35S promoter, specifically activated the $(Em)_2$-Gal4 binding site promoter (pZBL5) or the $(G-box)_4$-Gal4 binding site promoter (pZBL6) used to express the GUS reporter gene in stable transgenic tobacco seeds. As shown in FIG. 13, the level of gene activation conferred by combining G-box and Gal4 sites together (pZBL6) is much higher than that obtained from the Gal4 sites alone (pZBL3) (compare the level of GUS activity in lane N in FIG. 13 to that in lane N in FIG. 9). Lane Q shows the level of GUS activity in seed from a highly expressed Ph/P-GUS line. This is the control Ph/P-GUS line described earlier (Odell et al., 1994 Plant Phys. 106: 447) containing a −410 phaseolin promoter. Lane R shows GUS activity in seed from a highly expressed 35S-GUS line, which is derived from pZ41oxAG transformants described in Russell et al. 1992 Mol. Gen. Genet. 234: 49. The examples of the two component expression system demonstrated in FIG. 13 lane N, as well as in FIG. 14 lane O, and FIG. 15 lane P, had levels of expression that are higher than that of the phaseolin promoter. Many more examples in these figures had expression that is higher than that of the 35S promoter.

FIGS. 17–20 show activation of promoters containing an additional AT-rich enhancer from the 5' region of the phaseolin promoter located upstream of the Gal4 sites (pZBL7), the $(RY-G-Box-RY)_2$-Gal4 sites (pZBL8), the $(Em)_2$-Gal4 sites (pZBL9), or the $(G-box)_4$-Gal4 sites (PZBL10). The chimeric G4VP16 and G4Alf transcription factors, under control of either the phaseolin promoter or 35S promoter, specifically activated the Gal4 sites in pZBL7, pZBL8, pZBL9 and pZBL10 to express the GUS reporter gene in stable transgenic tobacco seeds. The level of GUS activities in $F_1$ seed resulting from crossing pZBL7, pZBL8, pZBL9 or pZBL10 plants to WT plants indicates the background level of expression from the GUS gene constructions in these plants. In the two component Gal4 system that includes seed-specific elements or constitutive elements and an AT-rich enhancer, the regulatory elements function together to further activate gene expression and increase the level of gene expression.

As shown in FIGS. 9–20, the levels of activation varied in crosses between different transformed lines. The highest activation was achieved when a Ph/P-G4VP 16 effector line (14A) or a Ph/P-G4Alf line (17A) was crossed with pZBL9 3F, 4F or pZBL10 11H, 7C reporter lines (FIG. 17, lanes L, N, T, Z, FIG. 19, lane L). The best gene expression level conferred by this two component Gal4 system in seeds was about 3-fold higher than that conferred by the phaseolin promoter (compare lanes L and A' in FIG. 17) and about 15-fold higher than the 35S promoter (compare lanes L and B' in FIG. 17). Similar, but a little lower levels of activation were achieved when 35S-G4VP16 and 35S-G4Alf were used as effectors (FIGS. 18 and 20).

Thus, the two component gene regulation system of the invention which is based on at least one Gal4 binding site and optionally additional regulatory elements, and the Gal4 DNA binding domain, in conjunction with an activation domain, was successful in activating gene expression in seed which harbor both components of the system. The most effective lines were able to direct expression at a 3-fold higher level than that obtained from the highly active phaseolin promoter.

Example 14

Assay of Transgene Expression in Seedlings $F_1$ tobacco seedlings from the genetic crosses were also analyzed for GUS activities. For each cross analyzed, about 50 seeds were germinated and grown on moistened sand at room temperature (20° C.) under fluorescent lights for 14 days. The seedlings (including both leaf and root tissue) were ground in 1.0 ml GUS lysis buffer. GUS assays and protein assays were done as described above. As shown in FIG. 21, both G4Alf and G4VP 16, driven by the 35S promoter, specifically activated gene expression in stable transgenic tobacco seedlings. The highest activation levels were achieved in the genetic cross between the 35S-G4VP16 effector lines and the PhG4G 17C reporter line (lanes O, P). The highest gene expression level conferred by this two component Gal4 gene expression system in tobacco seedlings was about the same level as conferred by the 35S promoter (compare lanes P and R). No activation above background was observed when no Gal4 binding sites are provided (-65-5C, lanes A-D). Specific gene activation was obtained in seedlings with 35S-G4Alf but to a less extent (lanes E-L). In all cases it can be seen that the use of different individual transformants for either the reporter or effector line results in differing activation levels. Those skilled in the art will recognize this as the manifestation of "position effects" commonly observed in families of transgenic plants (Jones et al., EMBO J. 4:2411–2418, 1985; De Almeida et al., MGG 218:78–86, 1989).

Thus, the two component gene regulation system of the invention which based on at least one Gal4 binding site and optionally additional regulatory elements and the Gal4 DNA binding domain, in conjunction with an activation domain, was successful in activating gene expression in seedlings which harbor both components of the system. The most effective lines were able to direct expression at the same level as obtained from the highly active 35S promoter.

What is claimed is:

1. A method for regulating gene expression in a stably transformed transgenic plant cell which comprises combining into the genome of the plant cell:
   a) a first chimeric gene comprising in the 5' to 3' direction:
      (1) a promoter containing at least one transcriptional regulatory element operably linked to at least one Gal4 binding sequence;
      (2) a coding sequence or a complement thereof operably linked to the promoter; and
      (3) a polyadenylation signal sequence operably linked to the coding sequence or a complement thereof;
      provided that when the promoter is a minimal promoter then both the transcriptional regulator element and the Gal4 binding sequence are located upstream of the minimal promoter; and
   b) a second chimeric gene comprising in the 5' to 3' direction:
      (1) a promoter;
      (2) a DNA sequence encoding a DNA binding domain of a Gal4 transcriptional activator;
      (3) a DNA sequence encoding a transcriptional activation domain operably linked to the DNA sequence of (2); and
      (4) a polyadenylation signal sequence operably linked to the DNA sequence of (3); wherein the expression of the second chimeric gene regulates expression of the first chimeric gene.

2. The method according to claim 1 wherein the transcriptional regulatory element is located upstream of the Gal 4 binding sequence when the promoter of the first chimeric gene is a minimal promoter.

3. The method according to claim 1 or 2 wherein the transcriptional regulatory element is selected from the group consisting of a seed-specific element or a constitutive element.

4. The method according to claim 3 wherein the transcriptional regulatory element further comprises an enhancer.

5. The method according to claim 1 or 2 wherein the transcriptional regulatory element is selected from the group consisting of RY-G-BOX-RY, Em, C1, Gy2, G-Box, CHS Unit 1 or the 5' enhancer of a phaseolin promoter.

6. The method according to claim 1, or 2 wherein first and second constructs are combined into the genome of the plant cell by (a) transforming a plant cell with the first construct, (b) transforming a second plant cell with the second construct, (c) growing fertile mature plants from the transformed plant cells in (a) and (b) and (d) genetically crossing the transformed plants to produce progeny whose genome contains the first and second constructs.

7. The method according to claims 1, or 2 wherein the transcriptional activation domain is an acidic transcriptional activation domain.

8. The method according to claims 1, or 2 wherein DNA sequence encoding the transcriptional activation domain is obtained from transcription factors selected from the group consisting of PvAlf or VP 16.

9. transformed plant having at least one gene whose expression is regulated using the method of claim 1, or 2.

10. Seeds obtained from the plant of claim 9.

* * * * *